(12) United States Patent
Yen et al.

(10) Patent No.: US 8,927,278 B2
(45) Date of Patent: Jan. 6, 2015

(54) METHOD FOR GENERATING IMMUNOMODULATORY CELLS, THE CELLS PREPARED THEREFROM, AND USE THEREOF

(75) Inventors: Lin-Ju Yen, Miaoli County (TW); Ko-Jiunn Liu, Miaoli County (TW); Huey-Kang Sytwu, Taipei (TW)

(73) Assignee: National Health Research Institutes, Zhuan Township (TW)

( * ) Notice: Subject to any disclaimer, the term of this patent is extended or adjusted under 35 U.S.C. 154(b) by 0 days.

(21) Appl. No.: 13/607,976

(22) Filed: Sep. 10, 2012

(65) Prior Publication Data

US 2014/0073569 A1    Mar. 13, 2014

(51) Int. Cl.
    *C12N 5/0783* (2010.01)
(52) U.S. Cl.
    CPC ............ *C12N 5/0636* (2013.01); *C12N 5/0637* (2013.01); *C12N 2501/12* (2013.01)
    USPC ............................................ 435/377; 514/9.5
(58) Field of Classification Search
    CPC ................. A61K 38/1833; A61K 2035/122; A61K 2035/124; C12N 2501/12; C12N 2502/1157; C12N 2506/11; C12N 2506/1392; C12N 5/0637; C12N 5/0636
    See application file for complete search history.

(56) References Cited

U.S. PATENT DOCUMENTS

| | | | | |
|---|---|---|---|---|
| 7,696,170 | B2* | 4/2010 | Amano et al. | 514/9.5 |
| 2006/0002932 | A1* | 1/2006 | Vieweg | 424/144.1 |
| 2008/0175825 | A1* | 7/2008 | Hampson et al. | 424/93.7 |

OTHER PUBLICATIONS

Rutella et al., Blood. Jul. 1, 2006;108(1):218-227.*
Soleymaninejadian et al., Am J Reprod Immunol. Jan. 2012;67(1):1-8.*
International Search Report and Written Opinion, PCT/US2013/058788, dated Oct. 17, 2013, 11 pages.
Di Nicola, M., et al., "Human bone marrow stromal cells suppress T-lymphocyte proliferation induced by cellular or nonspecific mitogenic stimuli," Blood, (May 15, 2002), vol. 99, No. 10, pp. 3838-3843.
Liu, K-J, et al., "Surface Expression of HLA-G Is Involved in Mediating Immunomodulatory Effects of Placenta-Derived Multipotent Cells (PDMCs) Towards Natural Killer Lymphocytes," (2011), Cell Transplantation, vol. 20, pp. 1721-1730.
Rasmusson, I., et al., "Mesenchymal stem cells inhibit lymphocyte proliferation by mitogens and alloantigens by different mechanisms," Experimental Cell Research, (2005), vol. 305, pp. 33-41.
Le Blanc, K., et al., "Mesenchymal Stem Cells Inhibit the Expression of CD25 (Interleukin-2 Receptor) and CD38 on Phytohaemagglutinin-Activated Lymphocytes," Scandinavian Journal of Immunology, (2004), vol. 60, pp. 307-315.
Yen, B.L., et al., "Isolation of Multipotent Cells From Human Term Placenta," Stem Cells, (2005), vol. 23, pp. 3-9.
Chang, C-J, et al., "Placenta-Derived Multipotent Cells Exhibit Immunosuppressive Properties That Are Enhanced in the Presence of Interferon-γ," Stem Cells, (2006), vol. 24, pp. 2466-2477.

* cited by examiner

*Primary Examiner* — Daniel C Gamett
(74) *Attorney, Agent, or Firm* — Baker & McKenzie LLP

(57) ABSTRACT

The present invention develops a straightforward and rapid method for generating immunomodulatory cells from peripheral mononuclear cells, comprising treating peripheral mononuclear cells with a hepatocyte growth factor (HGF) to induce differentiation of the peripheral mononuclear cells into immunomodulatory leukocytes. The present invention also provides an immunomodulatory cell prepared according to this method. The present invention further provides a method for treating a disease caused by abnormal immune response comprising administering a HGF to a patient exhibiting the disease, inducing the patient's peripheral mononuclear cells to differentiate into immunomodulatory leukocytes, and modulating the abnormal immune response.

11 Claims, 20 Drawing Sheets

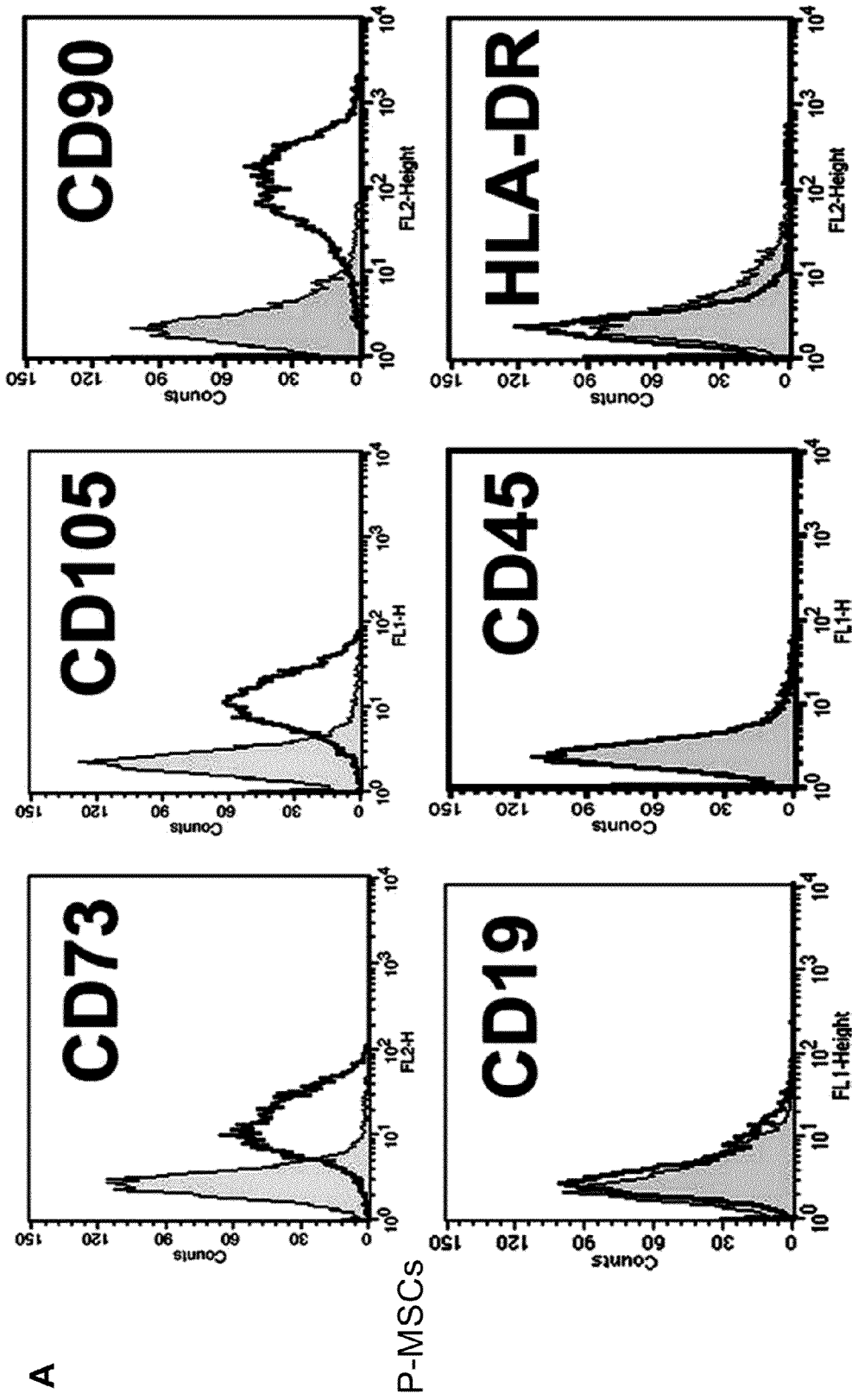
FIG. 1 (Continuous)

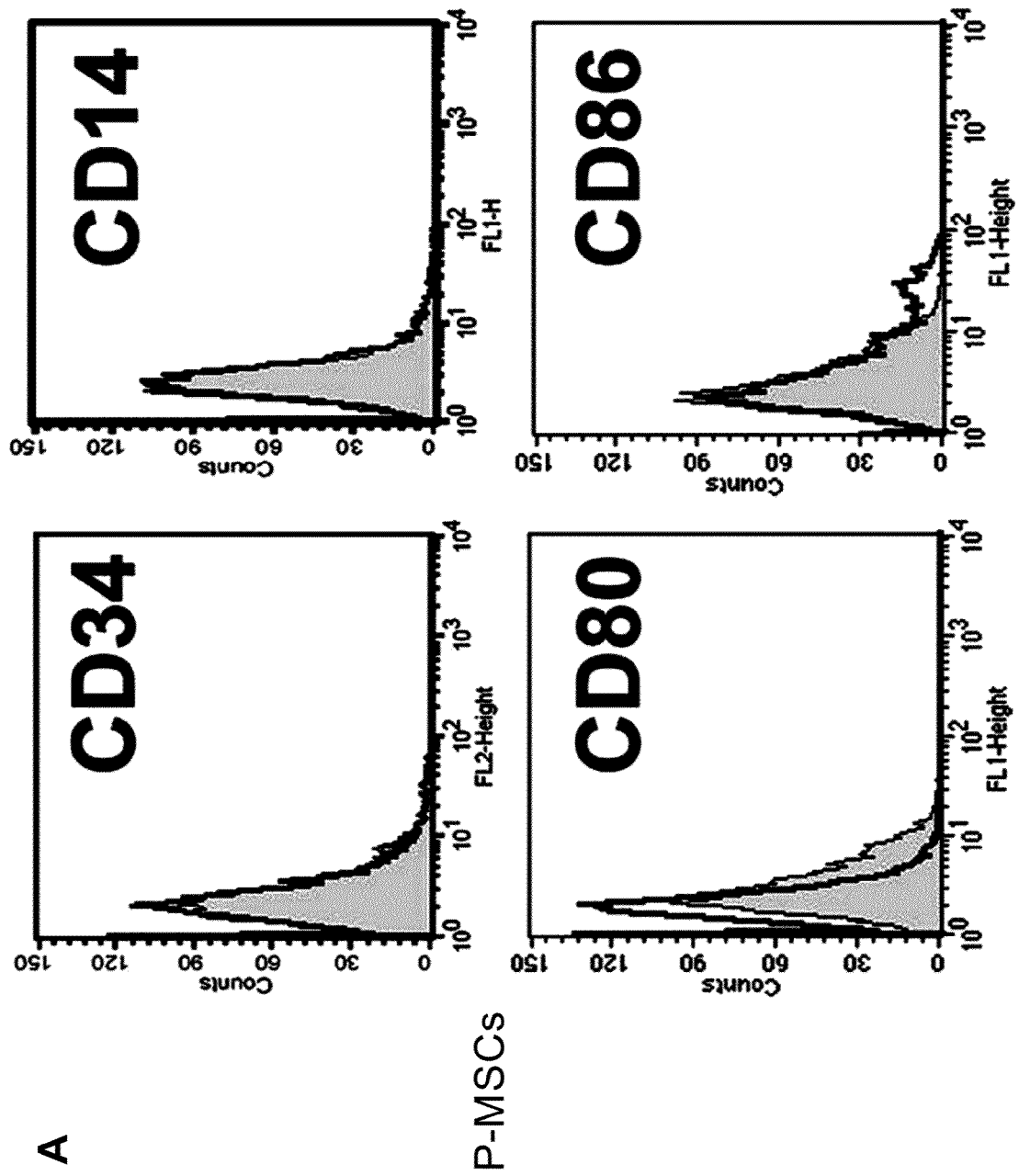
FIG. 1 (Continuous)

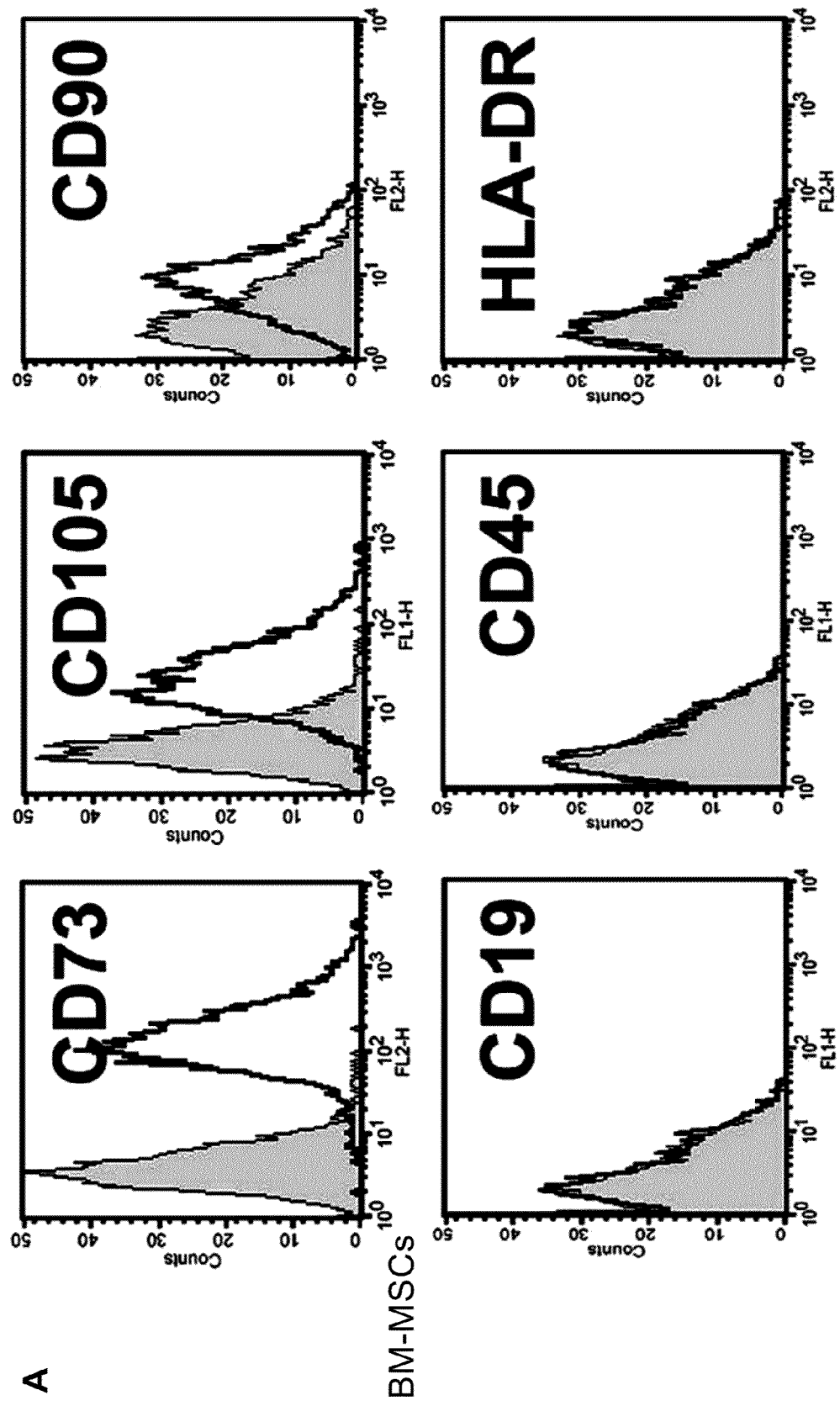
FIG. 1 (Continuous)

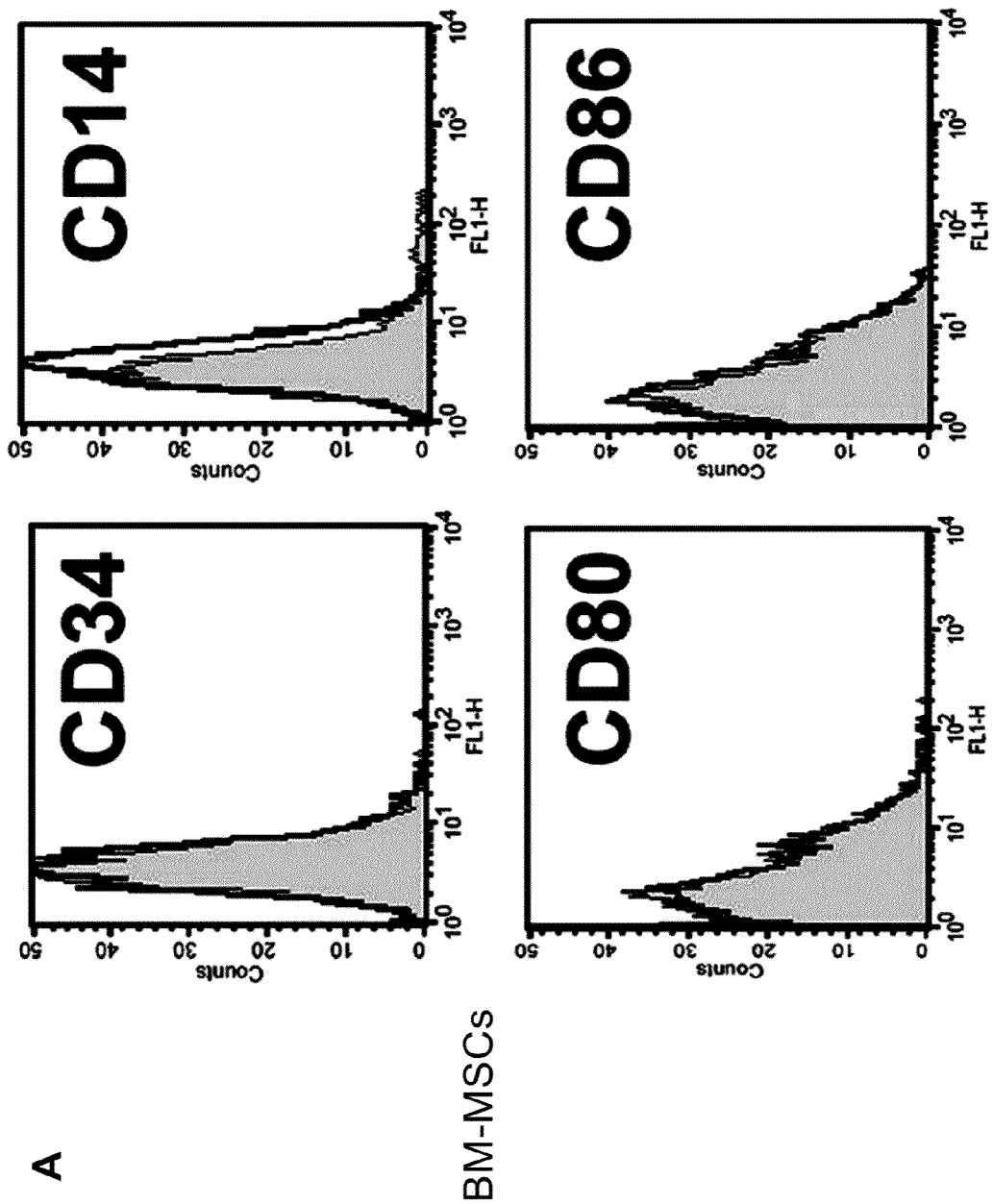
FIG. 1 (Continuous)

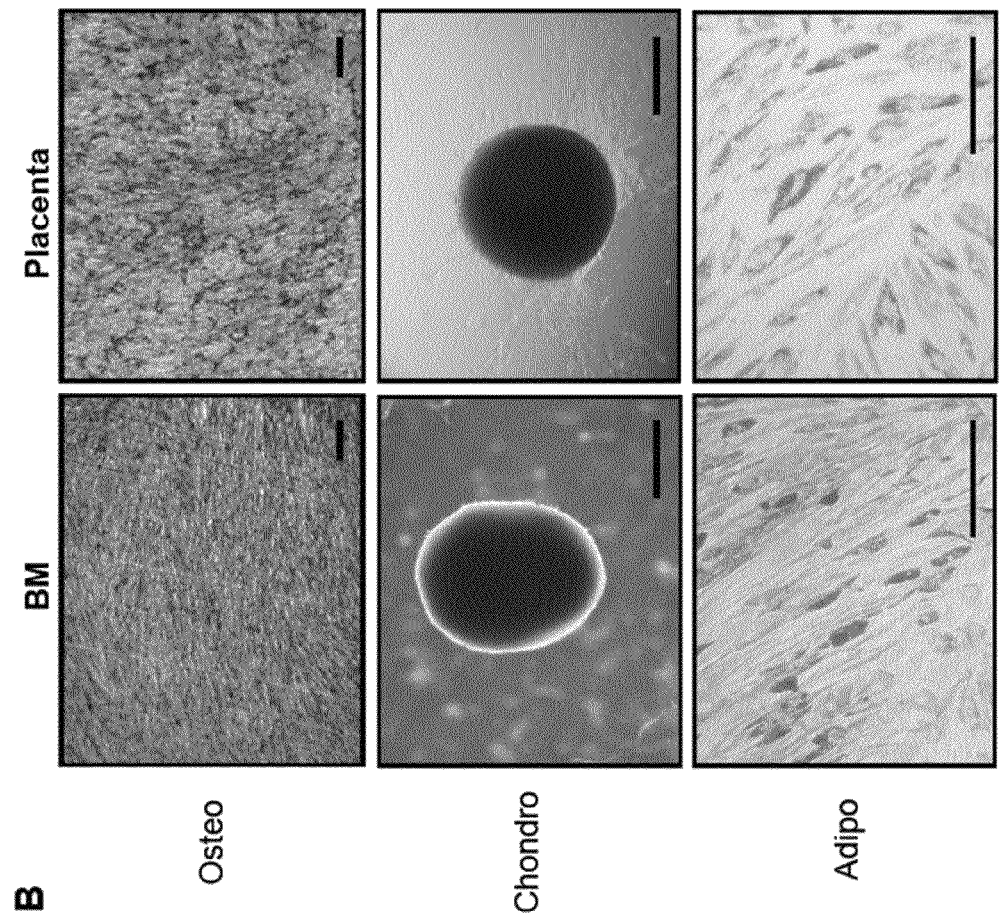
FIG. 1 (Continuous)

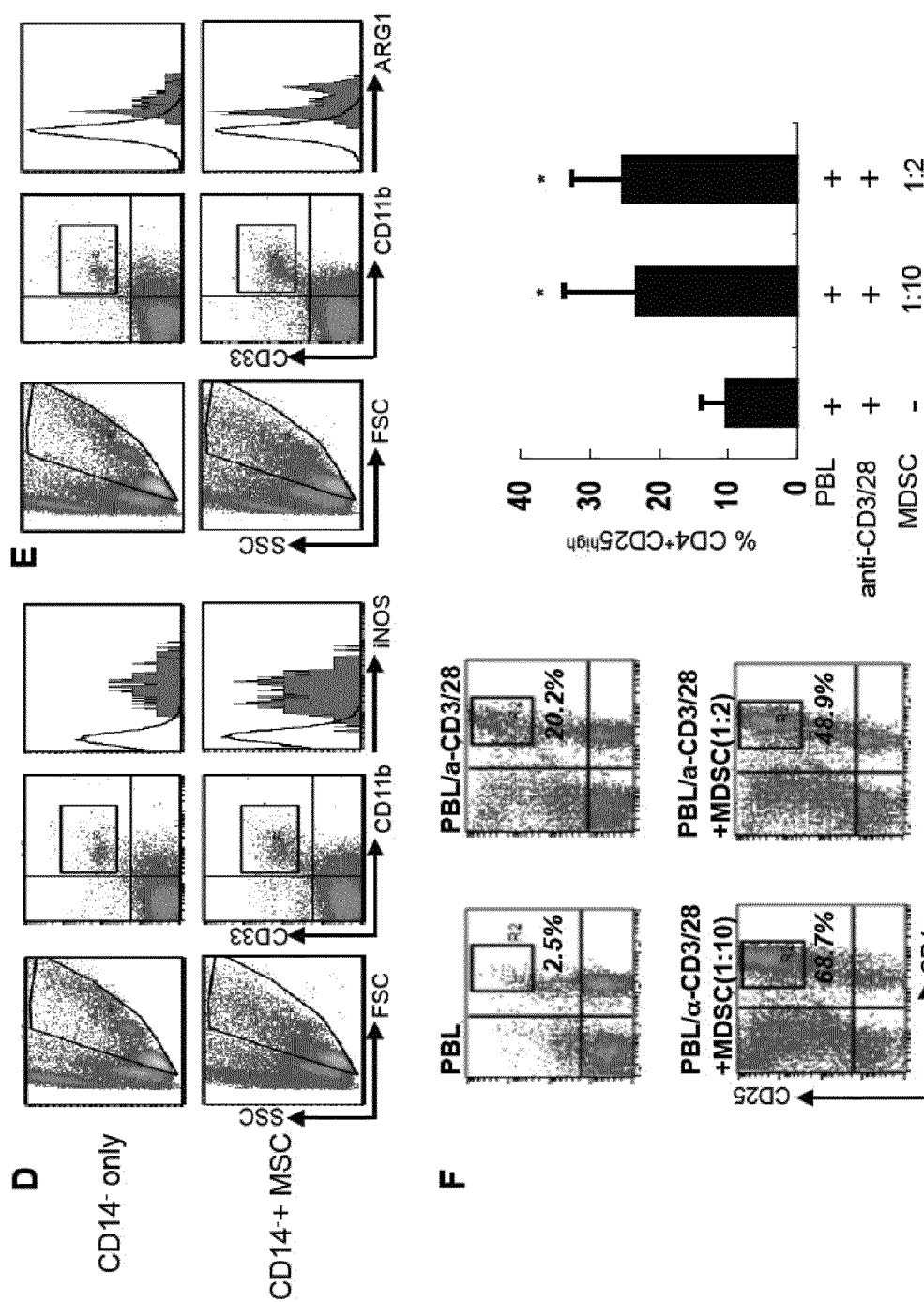
FIG. 2 Continue

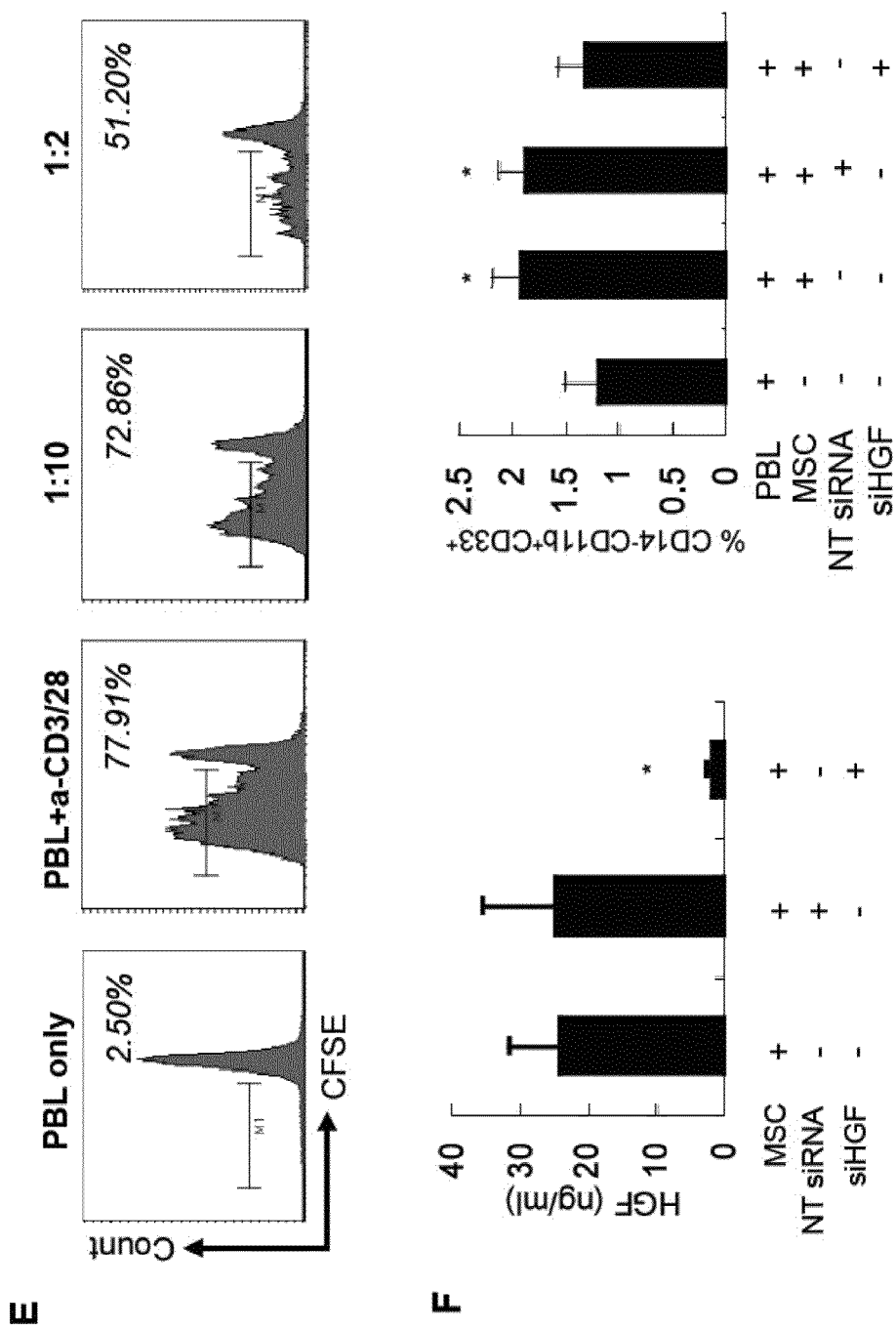
FIG. 3 Continue

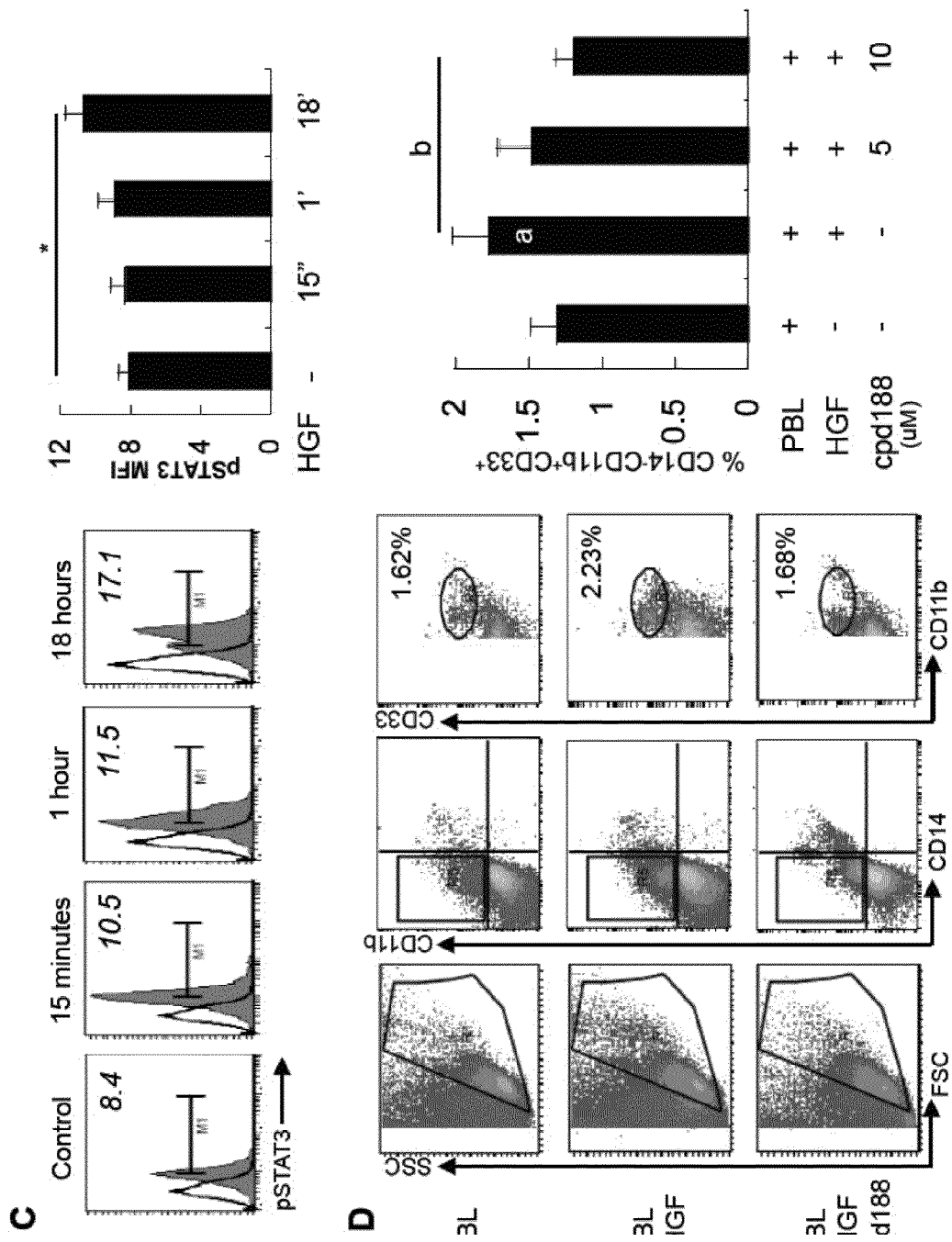
FIG. 5 Continue

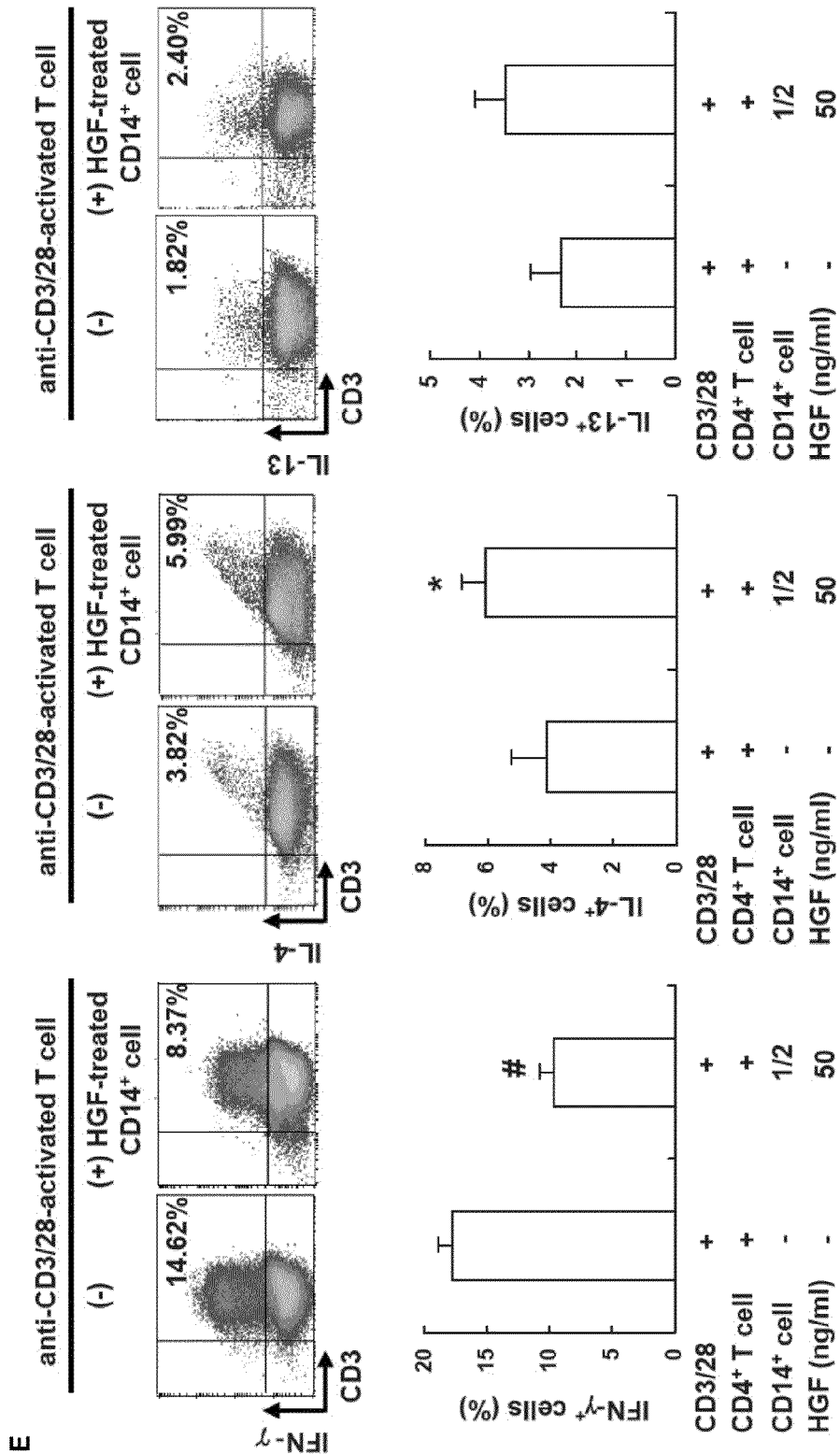
FIG. 8 Continue

```
                        SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
ctgtgaaaac aagagcaagg c                                              21

<210> SEQ ID NO 2
<211> LENGTH: 19
<212> TYPE: DNA
<213> ORGANISM: Artificial Sequence
<220> FEATURE:
<223> OTHER INFORMATION: PCR primer

<400> SEQUENCE: 2
gaagcttctg ttggctccc                                                 19

<210> SEQ ID NO 3
<211> LENGTH: 23
<212> TYPE: DNA
<213> ORGANISM: Artificial Sequence
<220> FEATURE:
<223> OTHER INFORMATION: PCR primer

<400> SEQUENCE: 3
tggcaccacc ttctacaatg agc                                            23

<210> SEQ ID NO 4
<211> LENGTH: 25
<212> TYPE: DNA
<213> ORGANISM: Artificial Sequence
<220> FEATURE:
<223> OTHER INFORMATION: PCR primer

<400> SEQUENCE: 4
gcacagcttc tccttaatgt cacgc                                          25
```

US 8,927,278 B2

METHOD FOR GENERATING IMMUNOMODULATORY CELLS, THE CELLS PREPARED THEREFROM, AND USE THEREOF

SEQUENCE LISTING SUBMITTED ON COMPACT DISC

The sequence listing in computer readable format is contained on a CD-R provided herewith under the file name "Sequence Listing.txt." This file is 2 kb and was created on Nov. 26, 2012 and saved to the "COPY 1 REPLACEMENT" and "COPY 2 REPLACEMENT" CDs on Mar. 12, 2013. The machine format is IBM-PC and the operating system compatibility is MS-Windows. Two copies of the CD-R containing the sequence listing in computer readable format are provided pursuant to 37 C.F.R. § 1.824. The complete contents of the CD-R are hereby incorporated by reference herein. A paper copy of the sequence listing is also provided.

CROSS-REFERENCE TO RELATED APPLICATIONS

Not applicable.

BACKGROUND OF THE INVENTION

The present invention relates to a method for generating cells with specific functions. In particular, the present invention relates to a method for generating immunomodulatory cells.

Autoimmune diseases arise from an inappropriate immune response of the body against substances and tissues normally present in the body. In other words, the immune system mistakes some part of the body as a pathogen and attacks its own cells. Rejection of transplantation is another problem caused by undesired immune response. Transplantation is the act of transferring cells, tissues or organs from one site to another. As transplantation becomes a routine medical treatment, the immune system remains the most formidable barrier.

Immune suppression drugs are generally applied for treatment/prevention of autoimmune diseases and transplantation rejection, which decrease the immune response. Immune suppression drug companies disclose various side effects, including suppressing the whole immune system and rendering the patient susceptible to infection. Biological agents are also applied to said treatment, including anti-cytokine therapy, T cell depletion therapy, B cell depletion therapy and tolerance induction therapy. Recently, cell therapy including providing adoptive T-cell or stem cell presents a new choice for treatment/prevention of autoimmune diseases and transplantation rejection but it is still developing.

Human mesenchymal stem cells (MSCs) are a population of multilineage progenitor cells with the ability to differentiate into multiple mesenchymal lineages. MSCs have been isolated from bone marrow (BM) and a number of other organs including adipose tissue, placenta, amniotic fluid, and fetal tissues such as fetal lung and blood. The ease of isolation along with reports of differentiation into extra-mesodermal cell types have made these post-natal progenitors a popular choice for cell therapy for a variety of diseases.

In addition to multilineage differentiation capacity, BM and fetal MSCs have been shown to harbor immunomodulatory effects. MSCs have been implicated in modulating the proliferative capacity and effector functions of T cells, B cells, monocyte-derived dendritic cells (DCs) and natural killer lymphocytes (NKs). The effects of human MSCs on immune cells are mainly mediated through cell contact-independent processes, however, the precise mechanisms are still unknown.

Research is increasingly showing the importance of immunomodulatory immune cells. A number of leukocyte subpopulations are now known to exert immunosuppressive effects, including regulatory T lymphocytes, type II macrophages, and immature DCs. Data regarding immunomodulatory monocytes, on the other hand, have been scarce.

Hepatocyte growth factor (HGF) is a well-known mitogen and a developmentally important molecule. Also known as scatter factor, HGF not only imparts strong growth signals but also induces cells to migrate; hence, HGF has been well studied in the context of cancer growth and metastasis. Less is known about its non-mitogenic effects. HGF is secreted by mesenchymal cells and targets and acts primarily upon epithelial cells and endothelial cells, and also upon haemopoietic progenitor cells. It has been shown to have a major role in embryonic organ development, in adult organ regeneration and in wound healing. It has been reported that a role for HGF and TGF-β as mediators for suppression of T-cell proliferation in a mixed lymphocyte reaction, which is proved by providing neutralizing antibodies against TGF-β and HGF, then the proliferative response of T cell being restored (Di Nicola et al., Blood 2002; 99:3838-3843). However, a different conclusion has been reported that these factors are unrelated to the suppressive effect by MSCs on T cells stimulated with mitogens and different mechanisms depending on the stimuli are suggested (Le Blanc et al., Scand J Immunol 2004; 60:307-315; Rasmusson I et al., *Exp Cell Res* 2005; 305:33-41). Accordingly, the functions and interactions between HGF and immune system are still unclear.

BRIEF SUMMARY OF THE INVENTION

The present application describes a method for generating immunomodulatory cells comprising treating peripheral mononuclear cells with a hepatocyte growth factor to induce differentiation of the peripheral mononuclear cells into immunomodulatory leukocytes.

The present application also describes an immunomodulatory cell prepared accordingly.

The present application further describes a method for treating a disease caused by abnormal immune response comprising administering a hepatocyte growth factor (HGF) to a patient exhibiting the disease, inducing the patient's peripheral mononuclear cells to differentiate into immunomodulatory leukocytes, and modulating the abnormal immune response.

BRIEF DESCRIPTION OF THE DRAWINGS

FIG. 1 shows characterization of bone marrow mesenchymal stem cells (BM-MSCs) and placenta-derived MSCs (P-MSCs). FIG. 1A: Surface marker profile and FIG. 1B: tri-lineage differentiation phenotype for BM-MSCs and P-MSCs. Osteo, osteogenic lineage; chondro, chondrogenic lineage; adipo, adipogenic lineage; scale bar, 200 mm.

FIG. 2A: Expansion of CD14–CD11b+CD33+ cells from PBLs by MSCs. Allogeneic PBL (30 donors) were co-cultured alone (top panel) or with MSCs (lower panel; 3 donors of BM-MSCs and 3 donors of P-MSCs); FIG. 2B: quantification of percentage of PBL CD11b+ (upper graph) or CD14–CD11b+CD33+ cells (lower graph) after co-culture with MSCs; *, p<0.05 compared to PBL only; FIG. 2C: Suppressive function of MSC-induced MDSCs. Allogeneic PBL (T, target cells) were stained with carboxyfluorescein succinimidyl ester (CFSE) for assessment of cell division and stimulated with anti-CD3/28 (a-CD3/28) without or with the addition of MSCexpanded MDSCs (E, effector cells) at various E:T ratios. Flow cytometric analysis to assess PBL cell division was performed. Chart (right) is a quantitative summary of the experimental results. *, p<0.05 for trend. FIG. 2D: Expression of inducible nitric oxide synthase (iNOS) and FIG. 2E: arginase 1 (ARG1) by MSC-expanded MDSCs. Negatively selected CD14− cells from PBL were cultured alone (top panels) or with MSCs (lower panels) and further stained with CD11b, CD33, and iNOS (FIG. 2D) or ARG1 (FIG. 2E). FIG. 2F: Expansion of CD4+CD25high regulatory T cells (Tregs) by MSC-expanded MDSCs. CD14−CD11b+CD33+ MSC-expanded MDSCs were sorted (FACS) and co-cultured with anti-CD3/28-stimulated allogeneic PBL at various ratios and assessed for induction of CD4+CD25high T cells. Chart (right) is a quantitative summary of the experimental results. *, p<0.05 compared to PBL/a-CD3/28.

FIG. 3A: MSC expansion of MDSCs is mediated by secreted factors. Allogeneic PBL were co-cultured with MSCs either in direct contact (MSC) or separated by Transwell (TW) and assessed for expansion of CD14−CD11b+CD33+ MDSCs; *, p<0.05 compared to PBL only; n.s., not significant. FIG. 3B: Highly secreted factors of MSCs as assessed by quantitative cytokine array; IL, interleukin; LAP, latency associated peptide; SDF, stromal-derived factor. FIG. 3C: Exogenous addition of recombinant HGF to PBL increases the number of MDSCs (*, p<0.05 for trend). FIG. 3D: Assessment of iNOS (top panel) and ARG1 expression (lower panel) in HGF-expanded MDSCs. FIG. 3E: Suppression of anti-CD3/28-stimulated PBL proliferation by HGF-expanded MDSCs as assessed by flow cytometric analysis of CFSE staining for cell division. FIG. 3F: Knockdown of HGF secretion in MSCs with HGF-specific small interfering RNA (siRNA) abrogates the expansion of MDSCs. Allogeneic PBLs were co-cultured with MSCs (3 donors) transfected with either non-target small interfering RNA (siRNA Ctrl) or HGF-specific siRNA (si-HGF) and assessed for CD14−CD11b+CD33+ cells; *, p<0.05 compared to MSC (left graph) or PBL only (right graph).

FIG. 4A: Level of HGF secretion by MSCs, MG63 (osteosarcoma cell line), embryonic stem cell-derived mesenchymal progenitors (EMP), and JEG-3 (choriocarcinoma cell line), and FIG. 4B: Fold-expansion of MDSCs after co-culture of the four cell types with PBL; *, p<0.05 for trend. FIG. 4C: Tail vein injection of recombinant HGF (100 ng) to C57BL/6 mice and assessment CD11b+Gr1+ cells in the peripheral blood, spleen, and bone marrow 1 day and 3 days after injection, *, p<0.05 compared to PBS.

FIG. 5A: Expression of c-met on MDSCs as assessed by flow cytometric analysis (12 donors); left chart, quantification of mean fluorescent intensity (MFI); *, p<0.05 compared to isotype control (Ctrl). FIG. 5B: Involvement of c-met in HGF mediated expansion of MDSCs. PBLs were blocked with isotype control antibodies (IsoAb) or c-met blocking antibodies (anti-c-Met), treated with recombinant HGF (20 ng/ml) and assessed for expansion of CD14−CD11b+CD33+ cells. FIG. 5C: Involvement of STAT3 in HGF mediated expansion of MDSCs. Recombinant HGF (20 ng/ml) was added to CD14-leukocytes and stained for CD11b, CD33, and phosphorylated STAT3 (pSTAT3) as assessed by flow cytometry (right upper value, MFI). Chart (right) is quantitative summary of MFI. *, p<0.05 for trend. FIG. 5D: Recombinant HGF (20 ng/ml) was added to PBL with and without addition of cpd188 (STAT3 inhibitor) at various doses and stained for CD11b, CD33, and pSTAT3 as assessed by flow cytometry. Chart (right) is quantitative summary of percentage of CD14−CD11b+CD33+pSTAT3+ cells. a, p<0.05 compared to PBL only; b, p<0.05 for trend.

FIG. 7A: PBLs were cultured alone (unstimulated; black bar), stimulated by phytohemagglutinin (PHA; white bar) or anti-CD3/28 activation beads (gray bar) and with or without MSC-conditioned medium (CM) or FIG. 7D: Recombinant human HGF (rhHGF); n=15. The proliferation of stimulated PBLs is set at 100%, which is defined as >90% of PBLs undergoing cell division as analyzed by flow cytometric analysis for carboxyfluorescein diacetate, succinimidyl ester (CFSE) staining. a, p<0.01; b, p<0.05, compared to control. c, p<0.05, compared to PHA-avtivated PBLs with MSC-CM in FIG. 7A. a, p<0.05; b, p<0.05, compared to PHA-avtivated PBLs with HGF in FIG. 7D. FIG. 7B: Cytokine production by MSCs (black bar), PBLs (white bar), PBLs cocultured with MSCs (gray bar), anti-CD3/28 activated PBLs (hatched bar), and anti-CD3/28 activated PBLs co-cultured with MSCs (dotted bar) as detected by quantitative cytokine array after 3 days of culture; n=1. FIG. 7C: Secretion of cytokines and stromal-related factors by MSCs as determined by quantitative cytokine array. FIG. 7E: HGF production in the CM of MSCs, MSCs after RNA silencing of HGF (HGF-siRNA), and MSCs after non-target siRNA as measured by enzyme-linked immunosorbent assay (ELISA); n=10. FIG. 7F: Proliferation of anti-CD3/28 activated PBLs cultured alone or with siRNA-transfected MSCs as assessed by flow cytometric analysis for CFSE after 72 hours; n=9. a, p<0.05, compared to anti-CD3/28-avtivated PBLs cultured with MSCs. Data are representative of 3 independent experiments unless otherwise noted, and shown as mean values±SEM. †, p<0.01; *, p<0.001, compared to control unless otherwise indicated by bars.

FIGS. 8A & 8B: c-Met expression on the T lymphocyte cell line (Jurkat), monocyte cell line (U937), and primary CD14+ cells (B; n=7) purified from PBLs; MFI, median fluorescence intensities. FIG. 8C: PBLs (white bar) or CD14+ cells-depleted PBLs (black bar) were cultured alone or stimulated by anti-CD3/28 beads with or without rhHGF; n=15. The degree of proliferation in rhHGF-treated PBLs is expressed as a percentage relative to anti-CD3/28-activated PBLs or CD14+-depleted PBLs. a, p<0.01; b, p<0.05, compared to anti-CD3/28-avtivated PBLs with HGF. FIG. 8D: Proliferation of CD4+ T cells cultured alone or stimulated by anti-CD3/28 with or without rhHGF-treated CD14+ cells (ratio of CD14+ to CD4+ T cells: 1/10, 1/5, 1/2 and 1/1) after 72 hours of co-culture. The proliferation of stimulated CD4+ T cells is set at 100%, which is defined as >90% of CD4+ T cells undergoing cell division as analyzed by flow cytometric analysis for CFSE staining. a, p<0.05 for trend. FIG. 8E: Intracellular production of IFN-, IL-4 and IL-13 in anti-CD3/28 activated CD4+ T cells co-cultured with or without rhHGF-treated CD14+ cells. The total number of T cells is set at 100%. Data are representative of 3 independent experiments unless otherwise noted and shown as mean values±SEM. #, p<0.05; *, p<0.001, compared to control unless otherwise indicated by bars.

FIG. 10A: Th1/2 cytokine profile by CD14+ cells alone (white bar) or co-cultured with MSCs (black bar) as detected by quantitative cytokine array after 3 days culture (n=1). FIG. 10B: IL-10 production by CD14+ cells treated with or without rhHGF, MSC- or siHGF-MSC-CM as measured by ELISA. FIG. 10C: IL-10-producing monocyte (IL10+CD11b+ cells) population in BM and splenocyte from mice injected with or without rmHGF. The total number of cells is set at 100%. Data are representative of 3 independent experiments and shown as mean values±SEM. #, p<0.05, compared to control unless otherwise indicated by bars.

FIG. 11A: IL-10 expression in U937 cells treated with or without rhHGF for the indicated time periods as detected by RT-PCR; β-actin, internal control. FIG. 11B: The expression of phosphorylated- (p-) ERK1/2, p-STAT3, p-p38, and p-AKT in U937 cells treated with or without rhHGF as detected by western blotting; ERK1/2, STAT3, p38, AKT, and α-Tubulin were used as internal controls. FIG. 11C: Gene expression of IL-10 by U937 cells with or without rhHGF treatment and pretreated with the ERK1/2 inhibitor U0126, p38 MAPK inhibitor SB203580, or STAT3 inhibitor cpd188 as detected by RT-PCR. FIG. 11D: Protein expression of IL-10 by U937 cells pretreated with the inhibitors U0126 or SB203580 and without (white bar) or with rhHGF (black bar); n=3; data shown as mean values±SEM. †, p<0.01; *, p<0.001, compared to control.

DETAILED DESCRIPTION OF THE INVENTION

Figure 2:
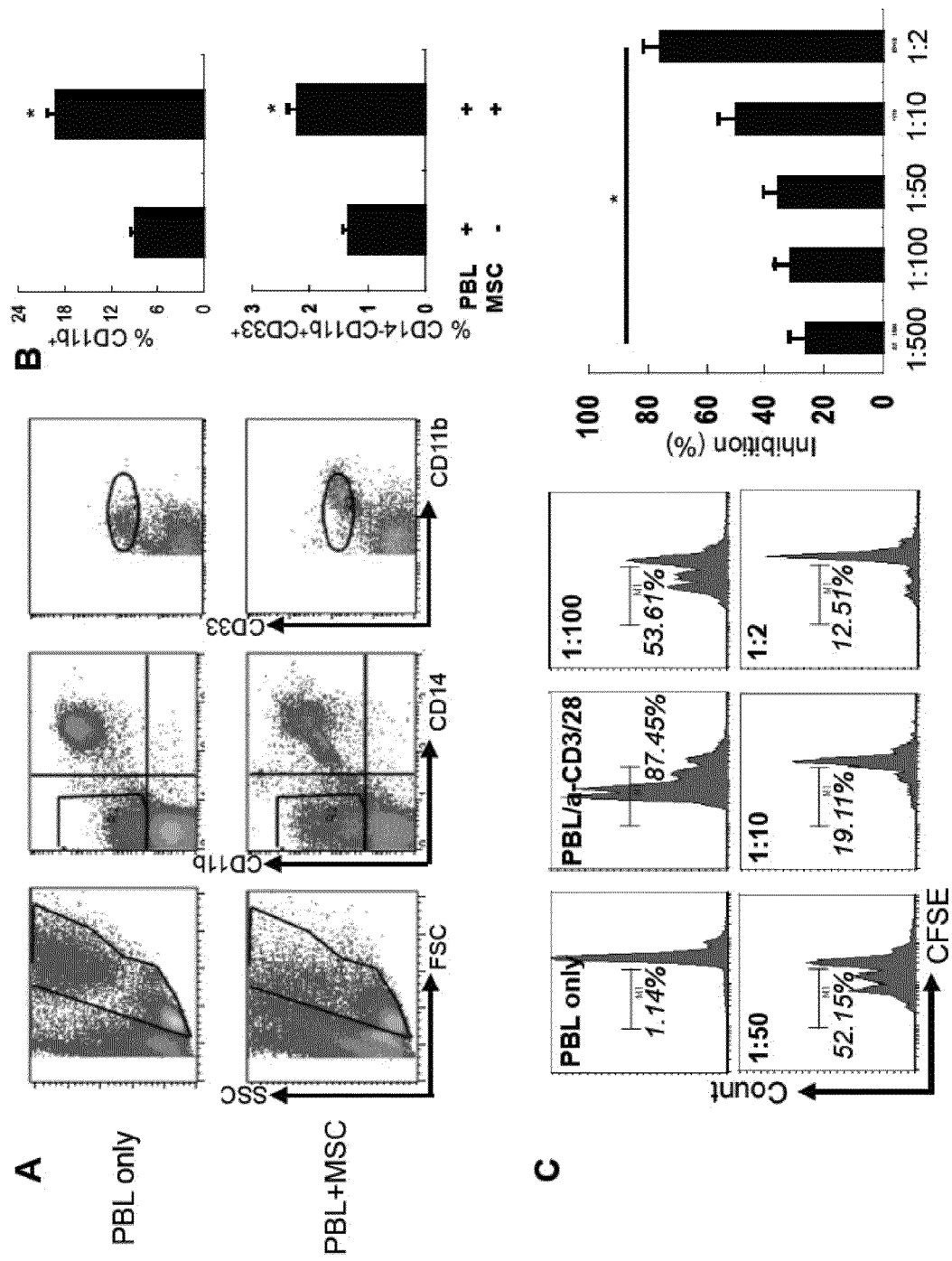
FIG. 2 shows MSCs expand the number of functional CD14–CD11b+CD33+ myeloid-derived suppressor cells (MDSCs) in allogeneic peripheral blood leukocytes (PBL).

The present application provides a method for generating immunomodulatory cells comprising treating peripheral mononuclear cells with a hepatocyte growth factor to induce differentiation of the peripheral mononuclear cells into immunomodulatory leukocytes.

The hepatocyte growth factor (HGF) can be a recombinant protein or a natural protein such as a protein produced by mesenchymal stem cells (MSC) or other cell lines. In one embodiment, HGF is from MSC. HGF is a secreted protein produced by MSC. In one embodiment, MSC is obtained from mammals including, but not limited to, humans, monkeys, mice, rats, swine, rabbits, dogs, cats and the like.

In the method of the present application, HGF treatment can be achieved by providing HGF as well as providing MSC to contact with the peripheral mononuclear cells. In one embodiment, the peripheral mononuclear cells can be co-cultured with MSC, which produces HGF and secretes it to environment.

The concentration of HGF for induction may be, for example but not limited to, between 3 to 40 ng per milliliter (ng/ml) of the medium. In one embodiment, the HGF concentration may be 5 ng/ml, 10 ng/ml, 15 ng/ml, 20 ng/ml, 25 ng/ml, 30 ng/ml, 40 ng/ml or between any two of those values. In one embodiment, 5-30 ng/ml is preferred, while 10-30 ng/ml is more preferred.

In the present application, the peripheral mononuclear cell means any blood cell has a round nucleus. The peripheral mononuclear cells contains lymphocytes, monocytes, macrophages, basophils and dendritic cells. The lymphocyte consists of T cells, B cells and NK cells. In one embodiment, the peripheral mononuclear cells are from a mammalian.

HGF induces the peripheral mononuclear cells to differentiate into immunomodulatory leukocytes such as a myeloid-derived suppressor cell (MDSC), a monocyte and the like. In one embodiment, the immunomodulatory leukocyte can suppress proliferation of an activated allogeneic lymphocyte.

The myeloid-derived suppressor cell (MDSC) has several immunomodulatory functions including, such as producing arginase, producing nitric oxide synthase, and inducing regulatory T cells. In one embodiment, the MDSC exhibits CD11b and CD33, and is CD14 negative, namely, the MDSC exhibits $CD14^-CD11b^+CD33^+$. In one embodiment, by using the method of the present application, the quantity of MDSC can be expanded 1.5 to 5 fold. In one embodiment, the MDSC occupies trace of the untreated peripheral mononuclear cells, such as about 1%, but is expanded to more than about 3% after treatment of HGF. In one embodiment, the MDSC can be expanded to occupy about 3-10% of the peripheral mononuclear cells, and about 3-5% is more preferred.

The monocyte has several immunomodulatory functions including, such as producing IL-10, producing an anti-inflammatory cytokine, modulating immune response toward Th2-dominant response, and the like. In particular, by using the method of the present application, the monocyte is induced to be able to produce IL-10 (i.e. IL10+). In one embodiment, the induced monocyte also exhibits CD14 and is CD16 negative, namely, the induced monocyte exhibits $CD14^+CD16^-IL10^+$. In one embodiment, the generated $CD14^+CD16^-IL10^+$ monocyte can be more than about 3% of the peripheral mononuclear cells by using the method of the present application while the untreated peripheral mononuclear cells contains none of $CD14^+CD16^-IL10^+$ but only $CD14^+CD16^-IL10^-$ monocyte. In one preferred embodiment, the $CD14^+CD16^-IL10^+$ monocyte is, based on the quantity of the peripheral mononuclear cells, about 5%.

The present application also provides an immunomodulatory cell prepared according to the above method. The immunomodulatory cell is derived from the peripheral mononuclear cell which is co-cultured with MSC and/or treated by an MSC-secreted HGF and therefore cell differentiation is induced. In one embodiment, the immunomodulatory cell is a $CD14^-CD11b^+CD33^+$ MDSC. In another embodiment, the immunomodulatory cell is a $CD14^+CD16^-IL10^+$ monocyte.

The present application develops a simple, straightforward, and rapid method to generate immunomodulatory cells from peripheral mononuclear cells. This methodology can be further used to generate immune-modulating cells for clinical application in autoimmune diseases and graft rejection after organ transplantation.

The present application further provides a method for treating a disease caused by abnormal immune response. Diseases caused by abnormal immune response include, but are not limited to, graft rejection of organ transplantation or autoimmune disease comprising system lupus erythematosus, multiple sclerosis, rheumatoid arthritis, type 1 diabetes mellitus, coeliac disease, Sjögren's syndrome, Hashimoto's thyroiditis, Graves' disease, idiopathic thrombocytopenic purpura, and the like.

In this treating method, HGF is administered to a patient exhibiting the disease. The patient can be a mammalian. In one embodiment, the administered HGF is in protein form, MSC-secreted HGF is preferred, and human-sourced MSC-secreted HGF is more preferred. In another embodiment, it is workable to administer a mesenchymal stem cell which generates HGF to the patient. After providing HGF, the patient's peripheral mononuclear cells can be induced to differentiate into immunomodulatory leukocytes such as MDSC, monocyte and the like. The immunomodulatory leukocytes derived from the cell differentiation exhibit various immune functions to regulate the patient's immune system, and the abnormal immune response can be modulated accordingly.

EXAMPLES

Example 1

Preparation of Immunomodulatory Myeloid-Derived Suppressor Cells

Material and Method
Cell Culture

Human placenta-derived MSCs—a population of MSCs from the term placenta—were isolated and expanded as previously described (Yen BL et al., *Stem Cells.* 2005; 23(1): 3-9; Chang C J et al., *Stem Cells.* 2006; 24(11): 2466-77; Liu K J et al., *Cell Transplant.* 2011; 20: 1721-30). Term (38-40 weeks gestation) placentas from healthy donor mothers were obtained with informed consent approved by the institutional review board. Briefly, MSCs were cultured in low glucose-Dulbecco's modified Eagle's medium (DMEM; Gibco-Invitrogen) with 10% fetal bovine serum (FBS; HyClone). Conditioned medium (CM) from MSC cultures at 70% of confluence were collected and stored at −80° C. until tested. Human peripheral blood lymphocytes (PBLs) from buffy coat samples chosen at random were obtained from healthy volunteers after informed consent as approved by the institutional review board. PBLs were separated by Ficoll-Paque (1.077 g/ml; Gibco-Invitrogen) density gradient centrifugation as previously described. $CD14^+$ and $CD4^+$ T cells were purified from PBLs by using the MACS (magnetic cell sorting) CD14 and CD4 Isolation Kits (Miltenyi Biotec) according to the manufacturer's instructions, respectively. Briefly, PBLs were incubated with the appropriate magnetic beads in 4° C. for 20 minutes. After the incubation, the PBLs and magnetic beads complex were washed with phosphate-buffered saline (PBS) containing 1% FBS and isolated to positive and negative fractions by AutoMACS (Miltenyi Biotec). The positive fraction was collected, and the purities of the $CD14^+$ and $CD4^+$ T cells were demonstrated to be greater than 98% by FACS analysis and cultured in RPMI-1640 medium.

Immunophenotyping

Flow cytometric analyses of cell surface markers were performed on a BD FACSCalibur flow cytometric system (BD Biosciences, Mississauga, Canada). All antibodies were purchased from BD Biosciences except for CD14, CD33, and CD11b from BioLegend (San Diego, Calif., USA); ARG1 from R&D Systems (Minneapolis, Minn., USA); iNOS from Abcam (Cambridge, UK); and c-met from eBiosciences (San Diego, Calif., USA).

Expansion of MDSCs

PBL were co-cultured with MSCs or cancer cell lines (10:1 ratio) for 3 days then assessed for CD14−CD11b+CD33−, which were the cell surface markers used also for FACS cell sorting of MDSCs with the BD Aria Cell Sorter (BD Biosciences). Some experiments were performed with magnetic bead-negatively selected CD14− cells according to manufacturer's instructions (Miltenyi Biotec, Bergisch Gladbach, Germany) instead of PBL. Recombinant human HGF (R&D Systems) was added to PBLs at the indicated doses. MDSC suppression analysis assessment of PBL cell division was performed as follows. Briefly, allogeneic PBL were labeled with 2.5 μmol/L of the fluorescent dye, carboxyfluorescein succinimidyl ester (CFSE; Molecular Probes/Gibco-Invitrogen, Grand Island, N.Y., USA) for 10 minutes, then stimulated with anti-CD3/CD28 beads (Gibco-Invitrogen). MSC-expanded MDSCs were sorted by FACS cell sorting for homogeneity then co-cultured with stimulated allogeneic PBL for 3 days at various effector-to-target (E:T) ratios. Flow cytometric analysis was performed to assess for PBL cell division in terms of CFSE dye intensity.

Quantification of HGF Secretion

Supernatants were collected from cell cultures for detection of HGF by using a commercially available ELISA kit (R&D Systems) according to manufacturer's instructions.

RNA Interference Experiments

Specific small interfering RNA (siRNA) for IL-6 and HGF were purchased from Gibco-Invitrogen and knockdown experiments were conducted according to manufacturer's instructions. The efficiency of siRNA knockdown of MSC-secreted factors was verified by ELISA.

In Vivo Experiments

All animal work was performed in accordance with protocols approved by the institutional Animal Care and Use Committee. C57BL/6 mice (four- to eight-week old) were obtained from the National Laboratory Animal Center of Taiwan (Taipei, Taiwan). Recombinant mouse HGF (100 ng, R&D Systems) was injected via tail vein, with mice sacrificed 3 days after injection. Peripheral blood, bone marrow, and spleen were collected for flow cytometric analysis of Gr1+ CD11b+ cells.

Statistical Analysis

In the above experiments, statistical analysis was performed with SPSS 18.0 software (SPSS Inc., Chicago, Ill., USA) with statistical significance defined as $p<0.05$. Student's t-test was used for comparisons between two groups, whereas ANOVA was used for comparison of multiple groups.

Example 1-(1)

MSCs can Expand High Numbers of Functional CD14−CD11b+CD33− MDSCs from PBLs

It has not previously been reported that the strong immunosuppressive properties of diverse sources of MSCs extend to involve the expansion of MDSCs. Both bone marrow and placental MSCs are positive for surface expression of CD73, CD105, and CD90 but negative for hematopoietic markers including the co-stimulatory molecules CD80 and 86 (FIG. 1A). Both populations of MSCs can differentiate into osteoblastic, chondrogenic, and adipocytic lineages, fulfilling the criteria for multipotent MSCs (FIG. 1B).

MSCs were co-cultured with allogeneic human PBLs and assayed for MDSCs, which in the human system are characterized as expressing CD33 and CD11b but not CD14. As shown in FIGS. 2A & 2B, both bone marrow and placental MSCs can increase the numbers of CD14−CD11b+CD33− cells from PBL. The properties and biological functions of MSC-expanded CD14−CD11b+CD33− cells ("MSC-induced MDSCs") are tested and the results are shown in FIGS.

2C-2F. MSC-induced MDSCs are functional to suppress lymphocyte proliferation by co-culturing in a dose-dependent manner (FIG. 2C). MSC-induced MDSCs can express AGR1 and iNOS (FIGS. 2D & 2E) and induce high numbers of CD4+CD25$^{high}$ Tregs from stimulated PBL (FIG. 2F) Thus, MSC-induced MDSCs have multiple immunomodulatory functions.

Example 1-(2)

Expansion of MDSCs by MSCs is Mediated by Secreted HGF

Figure 3:
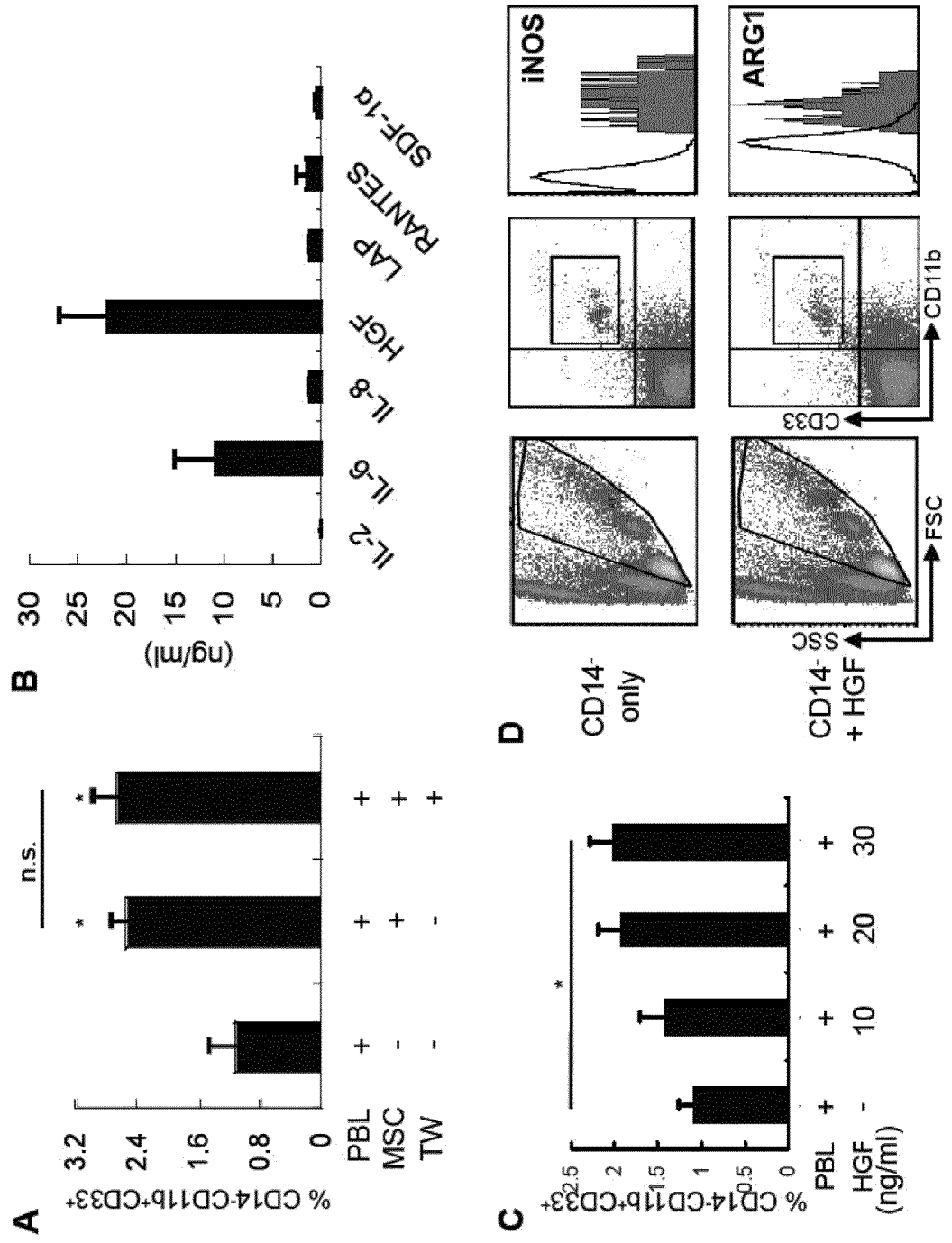
FIG. 3 shows MSC expansion of MDSCs is mediated by secreted hepatocyte growth factor (HGF).

As shown in FIG. 3A, the expansion of MDSCs by MSCs was not affected by transwell separation of cells, indicating that cell-cell contact was not needed and implicating secreted factors in this process. From analysis of the supernatant of MSCs, as shown in FIG. 3B, MSCs secrete a number of stromal-related factors such as RANTES/CCL5, HGF, and IL-6. IL-6 has been implicated in the expansion of MDSCs, however, using both blocking antibodies and siRNA knockdown studies, IL-6 did not contribute to the expansion of MDSCs by MSCs (data not shown).

Since HGF was highly secreted by MSCs, whether this molecule is involved in MSC expansion of MDSCs should be assessed. As shown in FIG. 3C, the addition of recombinant HGF can result in the expansion of MDSCs, and this effect is dose-dependent up to a concentration of 30 ng/ml of HGF, which is approximately the upper limit found in the conditioned medium of MSCs (FIG. 3B). HGF-expanded MDSCs also express iNOS and ARG1, as well as possess suppressive effector function (FIGS. 3D & 3E, respectively). To ascertain the involvement of HGF in MSC expansion of MDSCs, the secretion of HGF was suppressed by MSCs with RNA interference by siRNA. While secretion of HGF by MSCs was effectively suppressed, the expansion of MDSCs by MSCs was abrogated (FIG. 3F). Thus, the data supports that HGF secreted by MSCs is involved in the expansion of MDSCs.

Figure 4:
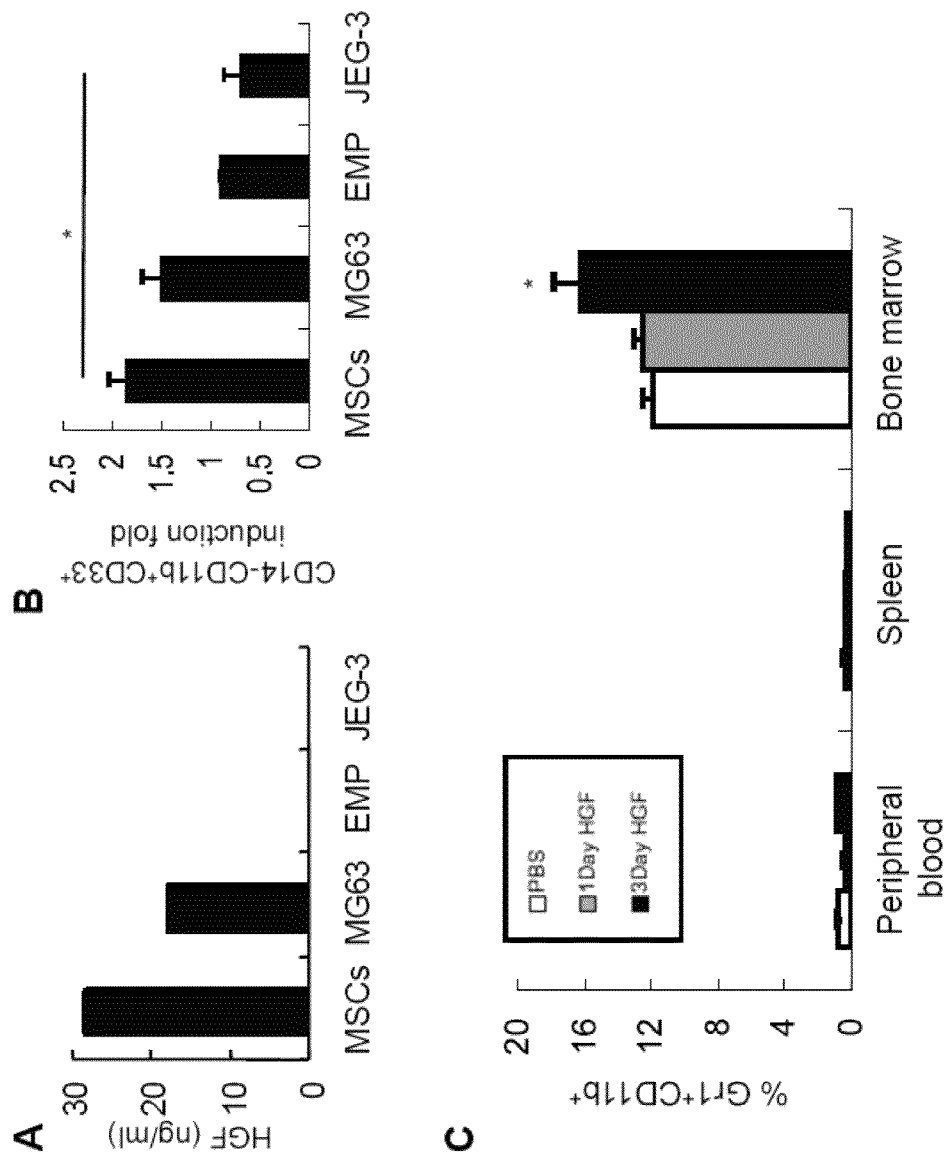
FIG. 4 shows cancer cell-secreted HGF and in vivo administration of HGF in mice can expand the numbers of MDSCs.

HGF from other cell lines were also tested. As shown in FIGS. 4A & 4B, the level of HGF secreted by several cell lines correlates with the number of MDSCs expanded.

To validate the findings in vivo, recombinant HGF was intravenously injected into wild type C57BL/6 mice. After 3 days, an increase of CD11b+Gr1+ MDSCs in the bone marrow of these mice can be observed (FIG. 4C), indicating that HGF can expand MDSCs in an in vivo setting.

Example 1-(3)

Expansion of MDSCs by HGF is Mediated Via c-Met, its Receptor, and Increased Phosphorylation of STAT3

Figure 5:
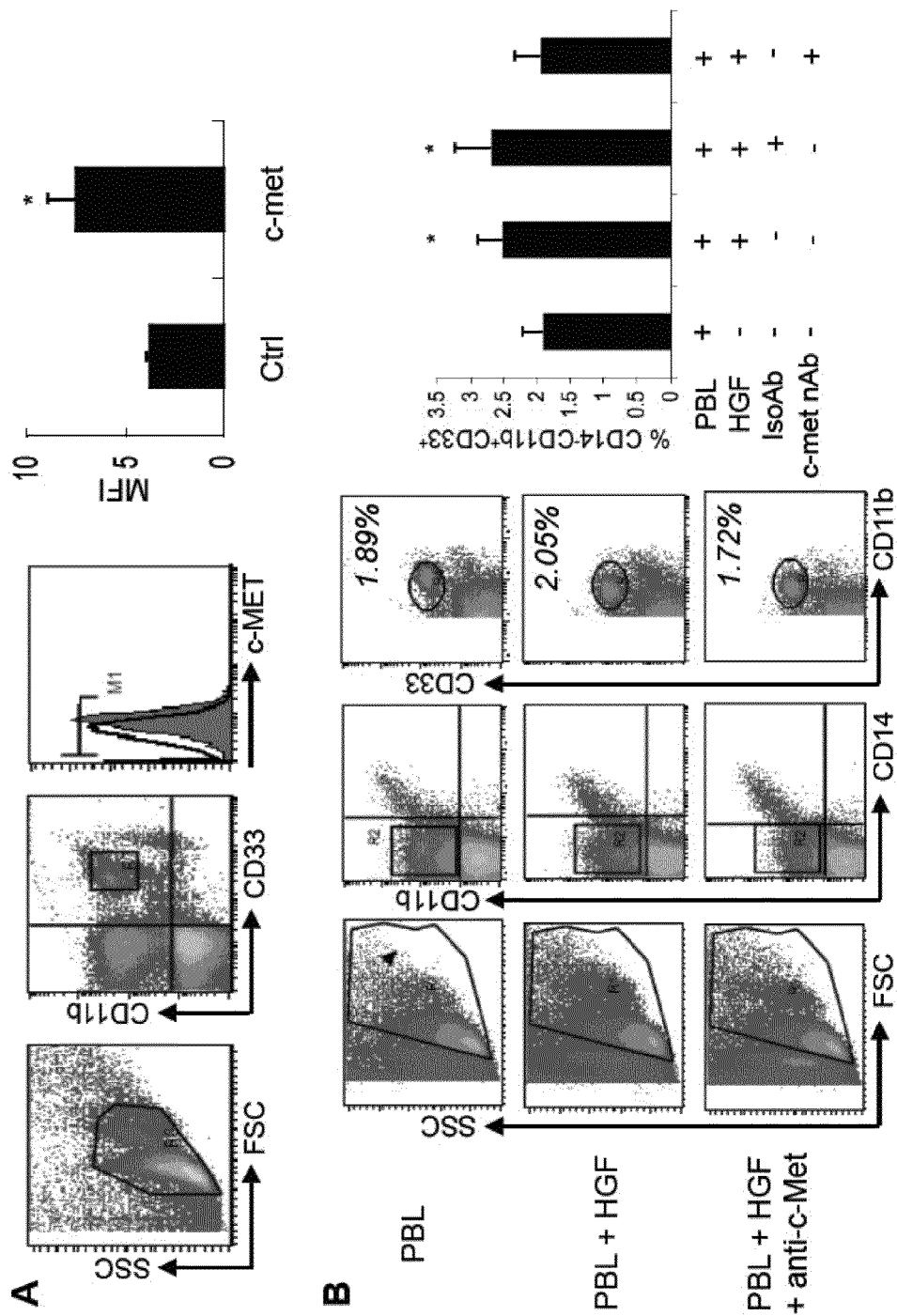
FIG. 5 shows expansion of MDSCs by HGF is mediated via c-met, its receptor, and increased phosphorylation of STAT3.

Further, the mechanism of HGF-mediated expansion of MDSCs is investigated. The expression of c-met—the cognate receptor for HGF—on MDSCs was examined, and it was found that CD14− leukocytes constitutively express low levels of c-met (FIG. 5A), and when c-met on CD14− cells was blocked with neutralizing antibodies, the expansion of MDSCs by HGF was abrogated (FIG. 5B). Then HGF-induced STAT3 phosphorylation in MDSCs was examined to confirm the effects of the HGF/c-met axis were mediated through STAT3. As shown in FIG. 5C, exogenous addition of HGF induces an increase over baseline levels of phosphorylated STAT3 (pSTAT3), which indicates activation of the pathway. When the STAT3 inhibitor cpd188 is added in the presence of exogenous HGF, the increased levels of pSTAT3 in MDSCs is abrogated in a dose-dependent fashion (FIG. 5D). Thus, HGF mediates the expansion of MDSCs by binding to its receptor c-met, which leads to increased phosphorylation of STAT3.

Figure 6:
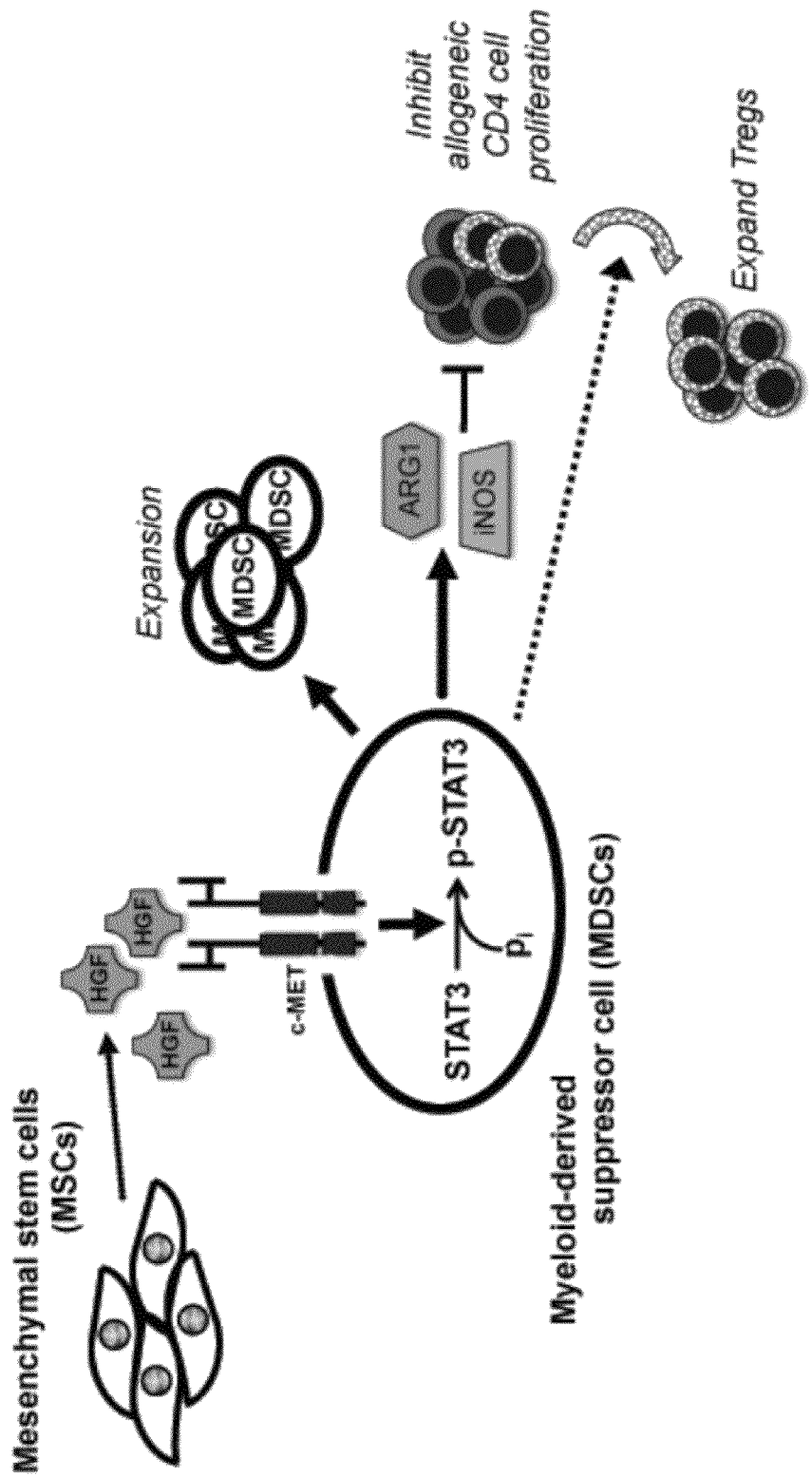
FIG. 6 shows mechanism of HGF-mediated expansion of MDSCs.

The mechanism of HGF-mediated expansion of MDSCs is shown in FIG. 6. HGF (especially secreted by MSCs) can lead to the expansion of MDSCs. Mechanistically, the expansion of MDSCs induced by MSCs is via the HGF/c-met axis with the downstream involvement of STAT3. MDSCs expanded by co-culture with MSCs or HGF are functional, expressing iNOS and ARG1, as well as harboring suppressive function and inducing Tregs. Therefore, HGF-induced MDSCs achieve immunomodulatory functions. Said immunomodulatory functions can be therapeutic for autoimmune diseases and other immune-related diseases such as graft-versus-host disease.

Example 2

Preparation of Immunomodulatory Monocytes

In the present application, it is found that MSCs can induce a population of immunomodulatory IL-10-producing CD14+ monocytes through secretion of hepatocyte growth factor (HGF). The presence of these immunomodulatory monocytes suppresses T cell proliferation as well as alter T cell effector function from a Th1 to Th2 profile. The interaction between HGF and CD14+ monocytes is also examined, and the signaling pathway involved in IL-10 production by these immunomodulatory monocytes.

Material and Method

Cell Culture

Human placenta-derived MSCs were isolated and expanded as described in Example 1.

Human histiocytic lymphoma cell line U937, and human acute T cell leukemia cell line Jurkat, were obtained from American Type Culture Collection (ATCC) and cultured according to published protocol. In some experiments, U937 were treated with ERK1/2 inhibitor U0126 (Cell signaling), p38 MAPK inhibitor SB203580 (Merck), and STAT3 inhibitor cpd188 (Merck) for 30 minutes before recombinant human HGF (rhHGF; Peprotech) treatment.

Cell Proliferation Assay

Cells were stained with 2.5 µM carboxyfluorescein diacetate, succinimidyl ester (CFSE; Gibco-Invitrogen) for 10 minutes at 25° C. in 0.1% bovine serum albumin (BSA). After washing twice with 0.1% BSA, the cells were resuspended in RPMI-1640 medium and incubated at 25° C. for another 10 minutes. PBLs or CD14-depleted PBLs were stimulated with human T-activator anti-CD3/CD28 Dynabeads (Gibco-Invitrogen) or mitogen phytohemagglutinin (PHA, 100 ng/ml; Sigma-Aldrich) with or without MSC culture medium and rhHGF. In addition, CD4+ T cells stimulated with anti-CD3/CD28 beads were co-cultured with rhHGF-treated HLA-mismatched CD14+ cells at different ratios. After 72 hours, the CFSE-labeled cells (5×105 cells/well) were harvested and washed twice with 0.1%. Analysis of cell division was performed by FACS as previously reported.

Cytokine Array

CM from of MSCs cultured with or without CD14+ cells were analyzed. Cytokine profiles were performed using Human Quantitative Antibody Arrays (RayBiotech) and processed according to the manufacturer's recommendation. Briefly, the membranes were blocked by incubation with the blocking buffer at room temperature for 30 minutes and incubated with the sample at room temperature for 90 minutes. Membranes were washed 3 times with Wash Buffer I and 2 times with Wash Buffer II at room temperature for 5 minutes per wash and incubated with biotin-conjugated antibodies at room temperature for 90 minutes. Finally, the membranes were washed and incubated with horseradish peroxidase-conjugated streptavidin at room temperature for 2 hours and with detection buffer for 2 minutes. A luminescence detector (GenePix 4000B Microarray Scanner, Axon Instruments, Inc.) was used for detection, with the data digitized and subjected to image analysis (GenePix Pro software, Axon Instruments, Inc.). Relative protein concentrations were obtained by subtracting the background staining and normalizing to the positive controls on the same membrane.

RNA Silencing

RNA silencing of HGF secretion in MSCs was performed by using two different HGF-silencing RNA (HGF siRNA) (Stealth Select RNAi™ siRNA, Gibco-Invitrogen) along with manufacturer recommended negative control siRNAs (Stealth™ negative control) according to manufacturer's recommendation. siRNAs were transfected into MSCs by using Lipofectamine™ RNAiMAX (Gibco-Invitrogen) following the manufacturer's recommended procedures. Briefly, the transfection mix was added to the cells 24 hours after plating in serum-free medium for 4 to 6 hours, and replaced with complete medium. After 3 days of culture, knockdown of HGF in MSCs was confirmed by ELISA of the CM. HGF and IL-10 enzyme-linked immunosorbent assay (ELISA) HGF production by MSCs and IL-10 production by monocytes/cell lines was measured by ELISA as previously reported and in accordance to the manufacturer's instructions (R&D systems).

Immunophenoyping

Cells (PBLs, CD14+ cells, leukemia cell lines) were stained for various surface expression and analyzed with a BD FACSCalibur (BD Biosciences) as previously reported. All antibodies for flow cytometry analysis except for c-Met (eBiosciences) were purchased from BD Biosciences. Each analysis included the appropriate FITC- and PE-conjugated isotype controls.

Intracellular Cytokine Staining

IFN-γ, IL-4 and IL13 production of anti-CD3/CD28 stimulated CD4+ T cells cultured with or without HGF-treated CD14+ cells were measured after 72 hours of incubation. Cells were re-suspended in the presence of 50 µg/ml phorbol 12-myristate 13-acetate (PMA; Sigma-Aldrich), 0.745 µg/ml ionomycin (Sigma-Aldrich) and 4 µM monensin (BioLegend) for 4-6 hours. Then, the cells were incubated with anti-human IFN-γ FITC (BioLegend), anti-human IL-4 PE (BioLegend) or anti-human IL13 PE (BD Biosciences) for 45 minutes at 4° C. FITC- and PE-conjugated isotype controls were used in parallel. The cells were washed twice, and suspended in PBS-BSA for FACS analysis.

In Vivo Recombinant Mouse HGF Challenge

Mice (C57BL/6) were injected intravenously with or without 200 ng of recombinant mouse HGF (rmHGF; Peprotech) diluted in 150 µl PBS. After 8 days, BM cells were extracted from mouse femurs by lavage with PBS, and spleens were removed, triturated at 4° C. with the end of a 3-ml syringe, and filtered through nylon mesh. The cell suspension was then centrifuged, red blood cells lysed, and the resulting single-cell suspension washed. B- and T-lymphocytes were depleted by magnetic sorting (auto-MACS) of splenocytes using CD45R/B220 PE (Biolegend, clone: RA3-6B2), CD90.2 PE (eBioscience, clone: 53-2.1), and anti-PE magnetic beads, respectively. The cell suspension was incubated with anti-mouse CD11b PE (BioLegend) and anti-mouse IL10 PerCPCy5.5 (BD Biosciences), and then detected by FACS.

RNA Isolation and Reverse Transcription-Polymerase Chain Reaction (RT-PCR)

Total RNA was extracted using Trizol reagent (Gibco-Invitrogen) and RT-PCR was performed as previously reported. The following PCR primers sets were used: IL-10, forward primer 5'-CTGTGAAAACAAGAGCAAGGC-3', reverse primer 5'-GAAGCTTCTGTTGGCTCCC-3' and β-actin positive control, forward primer 5'-TGGCACCAC-CTTCTACAATGAGC-3', reverse primer 5'-GCACAGCT-TCTCCTTAATGTCACGC-3'. Experiments were performed in triplicate. Relative mRNA levels were quantified by densitometric analysis using ImageJ software (NIH) and normalized against β-actin.

Western Blot Analysis

Protein was obtained from cells as previously reported. Primary antibodies against ERK1/2, STAT3, and α-Tubulin were obtained from Santa Cruz Biotechnology; and those for phospho-ERK1/2, phospho-STAT3, p38 MAPK, phospho-p38 MAPK, Aid, and phospho-Akt were obtained from Cell Signaling Technologies.

Statistical Analysis

Analysis of statistics was carried out using SPSS software (SPSS Inc., version 19.0) by using student's t tests for paired comparisons and ANOVA for multiple comparisons. All data are presented as mean±SEM, and p<0.05 was considered statistically significant. All experiments were performed at least in triplicate.

Example 2-(1)

HGF is Involved in Suppressing the Proliferation of Anti-CD3/28-Activated PBLs

Figure 7:
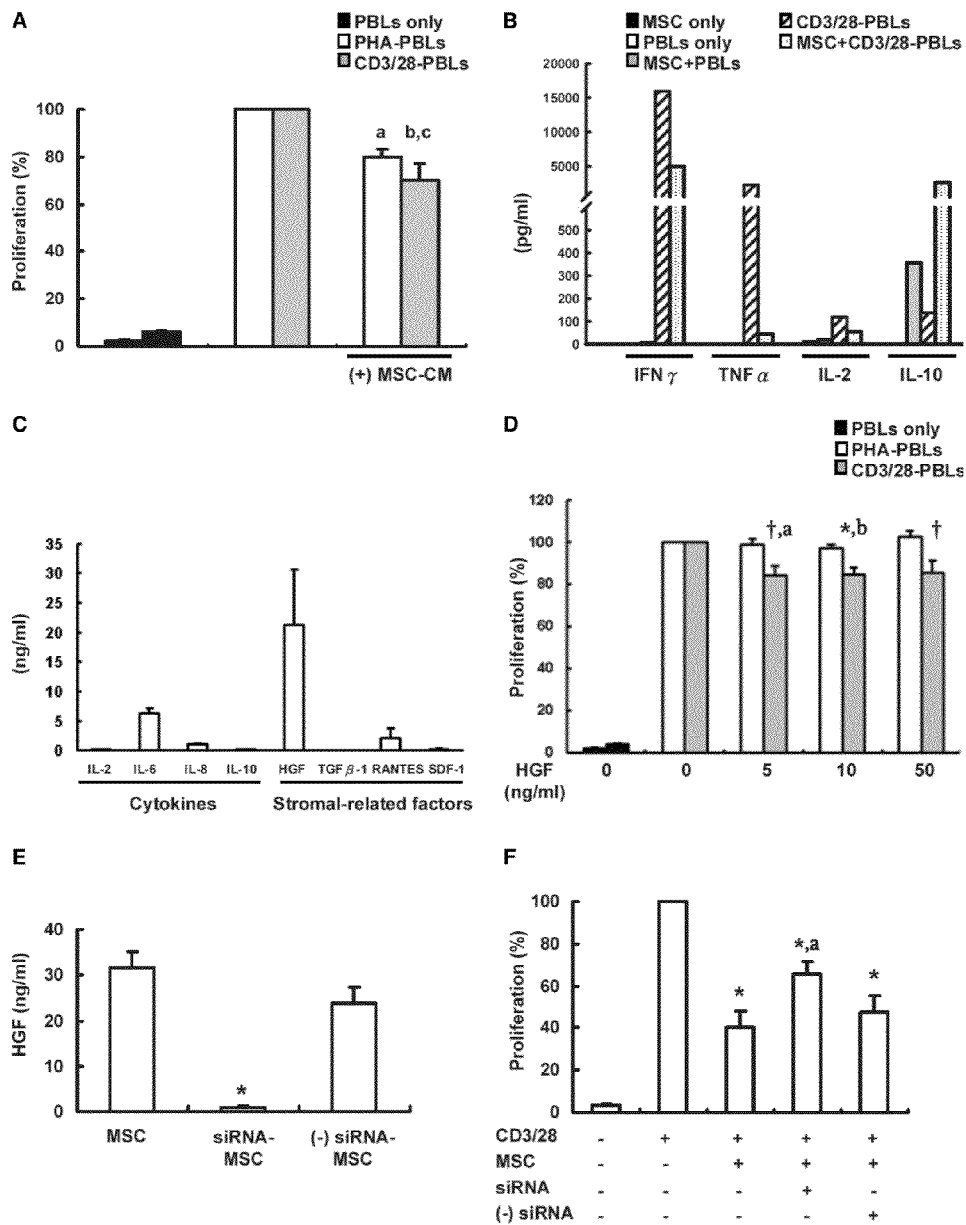
FIG. 7 shows hepatocyte growth factor (HGF) secreted by placenta-derived MSCs is involved in the suppression of anti-CD3/28-activated allogeneic peripheral blood lymphocytes (PBLs) proliferation.

As shown in Example 1, MSCs are strongly immunomodulatory towards T lymphocytes with effects mediated through secreted factors. As shown in FIG. 7A, the conditioned medium (CM) of MSCs (MSC-CM) can suppress the proliferation of PBLs activated with either PHA, which preferentially stimulate monocytes, or anti-CD3/28, which specifically stimulate T lymphocytes. MSC-CM exerted a slightly stronger suppressive effect on anti-CD3/28-stimulated PBLs than PHA-stimulated PBLs. Moreover, when anti-CD3/28-stimulated PBLs were co-cultured with MSCs, the cytokine profile is changed from a pro-inflammatory Th1 milieu—represented by IFN- and TNF- —to a more immunomodulatory milieu—represented by IL-10 (FIG. 7B).

Of the various cytokines, chemokines, and stromal-related molecules assayed (FIG. 7C), HGF is the most highly secreted molecule in MSC-CM. Then rhHGF was added to activated PBLs. It was unexpected that rhHGF can suppress the proliferation of PBLs activated by anti-CD3/28 but not by PHA (FIG. 7D), suggesting that the immunosuppressive effects of HGF are directed at T lymphocytes. Interestingly, there is no dose-dependent effect of HGF on suppressing PBL proliferation. Further, HGF knockdown experiments in MSCs by siRNA was performed, and the ELISA result was shown in FIG. 7E. When anti-CD3/28-activated PBLs were co-cultured with siHGF-MSCs, the immunosuppression was reversed to a significant extent (FIG. 7F). In addition, culture medium of HGF-siRNA MSCs also partly restored the proliferation suppression of PBLs (data not shown). These results collectively indicate that MSC-secreted HGF is involved in the suppression of anti-CD3/28-activated PBL proliferation.

Example 2-(2)

Figure 8:
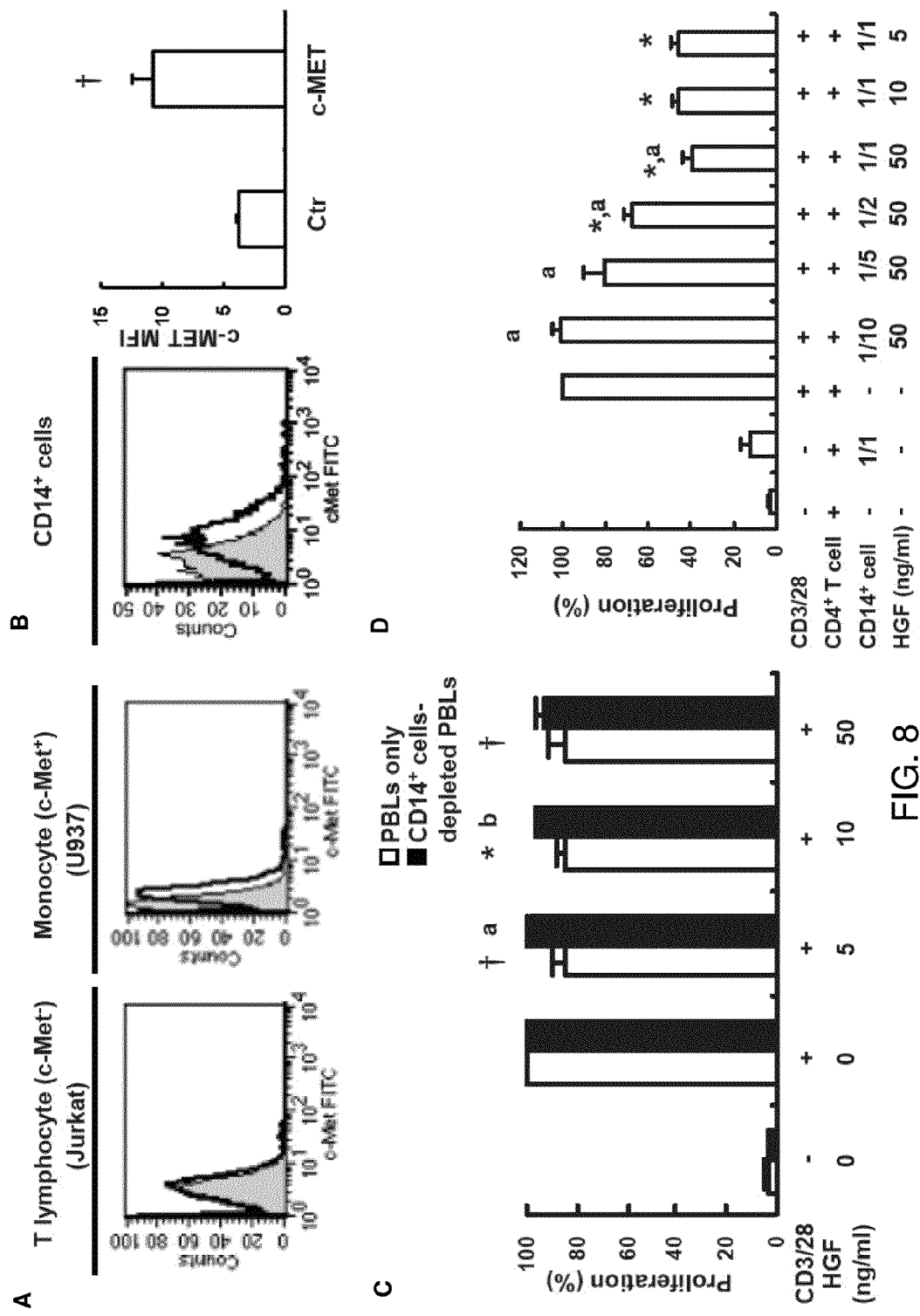
FIG. 8 shows CD14+ monocytes are required for the immunomodulatory effects of HGF on T lymphocyte function.

CD14+ Monocytes are Required for HGF-Mediated Immunomodulatory Effects on Activated CD4+ Cells HGF is the ligand for c-Met, a tyrosine-kinase receptor. Based on suppressive results of HGF on anti-CD3/28-activated but not PHA-activated PBLs, it appears that the immunomodulatory effects of HGF target T cells. However, c-Met did not express on primary T cells (data not shown) or on Jurkat cells, a T cell leukemia cell line (FIG. 8A). It has been previously reported that T cells do not express c-Met, but monocytes express low levels of this receptor. Monocytes, which are CD14+ cells, comprise about 10% of human PBLs, and it was found that the human monocytic leukemia cell line U937, as well as primary CD14+ monocytes from donor PBLs, express c-Met (FIGS. 8A and 8B).

These results suggest that the effects of HGF on T cells may require monocytes to act as an intermediary. To test this hypothesis, CD14+ cells were depleted from PBLs and then rhHGF was added to anti-CD3/28-activated PBLs. As shown in FIG. 8C, the suppressive action of HGF on proliferation of the anti-CD3/28 stimulated PBLs was completely abolished when CD14+ cells were depleted.

The CD14+-bead selected monocytes were treated with rhHGF and co-cultured with anti-CD3/28-stimulated CD4+ cells. As shown in FIG. 8D, T-cell proliferation can be inhibited by HGF-treated CD14+ cell, and the suppressive effects were increased as the ratio of effector to target cell (CD14+ to CD4+ cells response) was increased. However, the dose of HGF did not have an effect on the monocyte-mediated suppression, as same as FIG. 7D. Co-culture of anti-CD3/28-activated PBLs with HGF-treated CD14+ monocytes changed the cytokine profile from a more Th1 toward a Th2 profile (FIG. 8E). FACS analysis of intracellular Th1 (IFN-γ) and Th2 (IL-4 and IL-13) production in CD4+ T cells showed that IL-4 and IL-13 productions were enhanced when CD4+ T cells were co-cultured with HGF-treated CD14+ cell. In contrast, IFN-γ production was decreased. These data show that HGF interacts directly with CD14+ monocytes to alter T cell effector function.

Example 2-(3)

HGF Significantly Induces IL-10 Production

Figure 9:
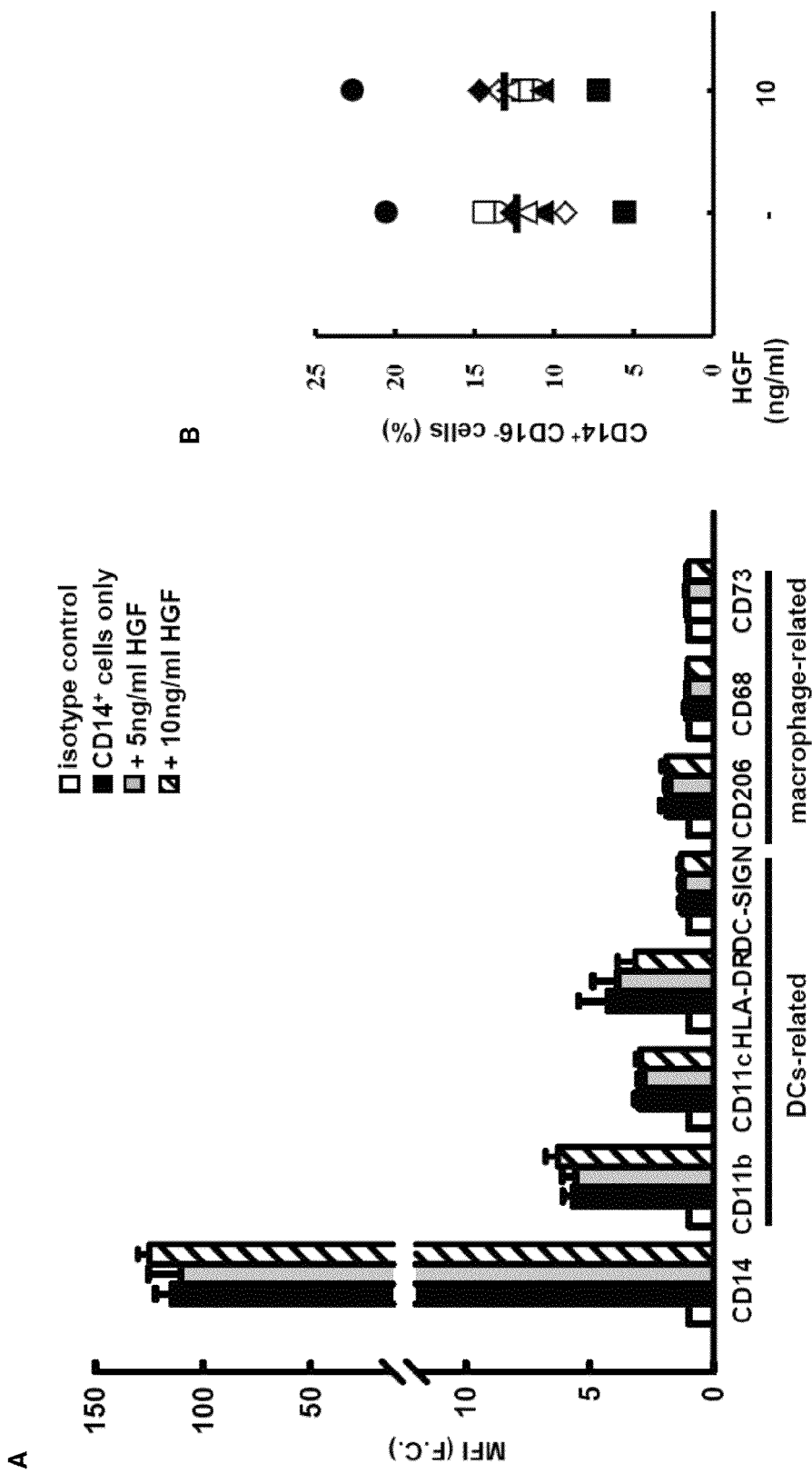
FIG. 9A shows dendritic cells (DCs) and macrophage-related surface markers expression on CD14+ cells treated with (gray and hatched bar) or without rhHGF (black bar) as detected by flow cytometricanalysis after 72 hours. The expression (MFI, median fluorescence intensities) of isotype-controls (white bar) is set at 1. Data are representative of 3 independent experiments and shown as mean values±SEM.
FIG. 9B shows CD14 and CD16 expression on PBL streated with or without rhHGF as detected by flow cytometricanalysis; n=8.

Monocytes are a major component of the cellular influx into an inflammatory environment, differentiating into DCs or macrophages with either pro- or anti-inflammatory properties, depending on the environmental stimuli. To investigate whether HGF modulates CD14+ monocyte differentiation, change of surface marker expression towards the DC and macrophage lineages was analyzed. After HGF treatment, there was no change in the expression level of either DC-related markers of CD11b, CD11c, and HLA-DR or macrophage-related markers of CD206 (FIG. 9A). In addition, no expression of DC-SIGN, CD68 and CD73 was detected. However, the fraction of CD16– cells were slightly increased (FIG. 9B), and the subset of CD14+ monocytes have been reported to be immunomodulatory.

Figure 10:
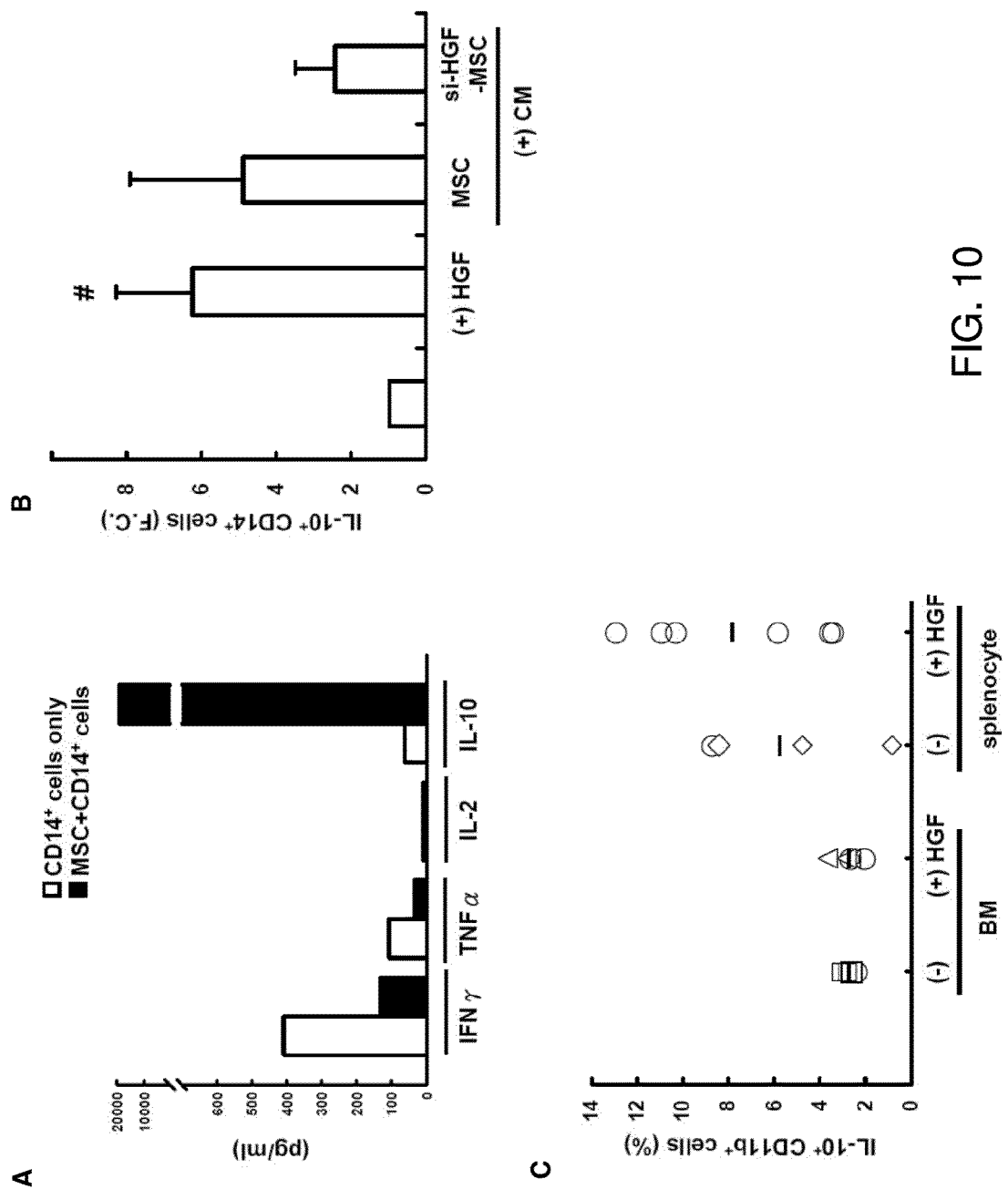
FIG. 10 shows HGF increases IL-10 production in monocytes.

In FIG. 10A, quantitative cytokine array analysis of CD14+ cells co-cultured with MSCs shows a significant reduction in production of pro-inflammatory cytokine including IFN-γ and TNF-α, and a significantly increase of the anti-inflammatory cytokine—IL-10. The data shows that immunosuppressive effects of MSCs can be due to the reduction of IFN-γ and the increased production of IL-10. To further determine the interaction between HGF and increased IL-10 production of monocytes, primary CD14+ cells were cultured with rhHGF and the IL-10 concentration in the culture medium was measured. As shown in FIG. 10B, CM from HGF-treated CD14+ cells as well as MSC-CM-treated CD14+ cells had high levels of IL-10 production above baseline levels.

mHGF was injected into wild-type B6 mice to test these effects in vivo. As shown in FIG. 10C, HGF induces a slight increase in IL-10-producing monocytes population in splenocytes, but not BM cells or peripheral blood (data not shown). Thus, HGF is involved in the production of IL-10 from CD14+ monocytes.

Example 2-(4)

HGF Induces Secretion of IL-10 Via ERK1/2 Phosphorylation

Figure 11:
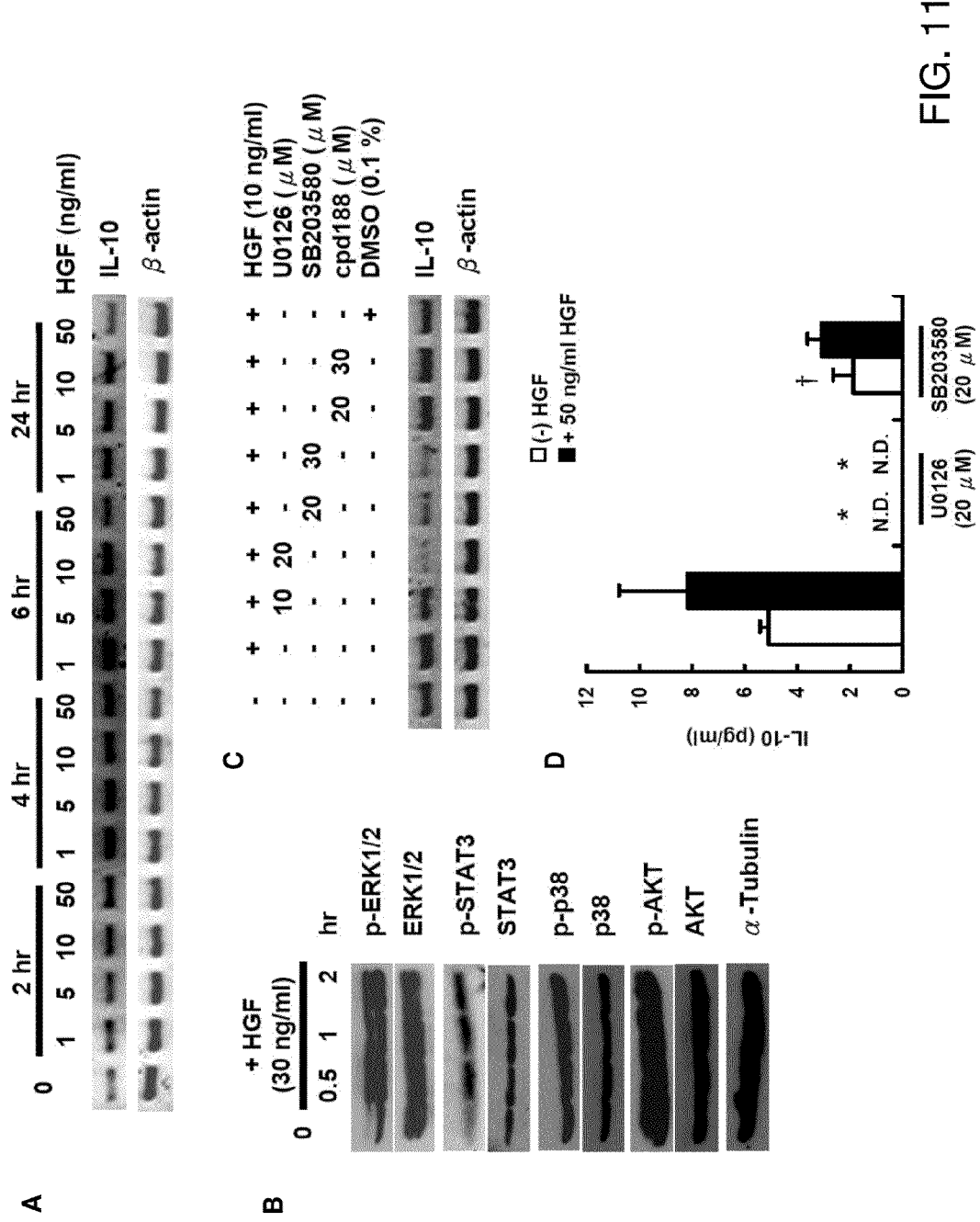
FIG. 11 shows HGF-induced production of IL-10 by CD14+ monocyte is mediated through ERK1/2 pathway.

Further, the mechanism of the production of IL-10 in monocytes induced by HGF is investigated. The monocytic cell line U937 cells was treated with HGF and changes in gene expression of IL-10 were assessed. As shown in FIG. 11A, an increase in IL-10 transcripts, which peaked at 6 hrs of rhHGF treatment, suggested that HGF may be directly responsible for IL-10 production. HGF triggers many intracellular signaling pathways, and of these downstream pathways, PI3K/AKT, Ras/ERK1/2, p38/MAPKs, and STAT3 are also involved in mediating IL-10 gene expression. As shown in FIG. 11B, phosphorylation of ERK1/2, STAT3, and p38/MAPK but not AKT is enhanced after HGF treatment of U937 cells. To further assess these three pathways, U937 cells were simultaneously treated with HGF and specific inhibitors: U0126 (p-ERK1/2 inhibitor), SB203580 (p38/MAPK inhibitor), and cpd188 (pSTAT3 inhibitor). As shown in FIGS. 11C and 11D, IL-10 gene expression was abrogated in a dose-dependent manner in U0126 and SB203580 groups, but only ERK1/2 inhibition resulted in a significant reduction of IL-10 protein production after HGF treatment. These results show that HGF-mediated monocyte production of IL-10 is mediated through ERK1/2.

Figure 12:
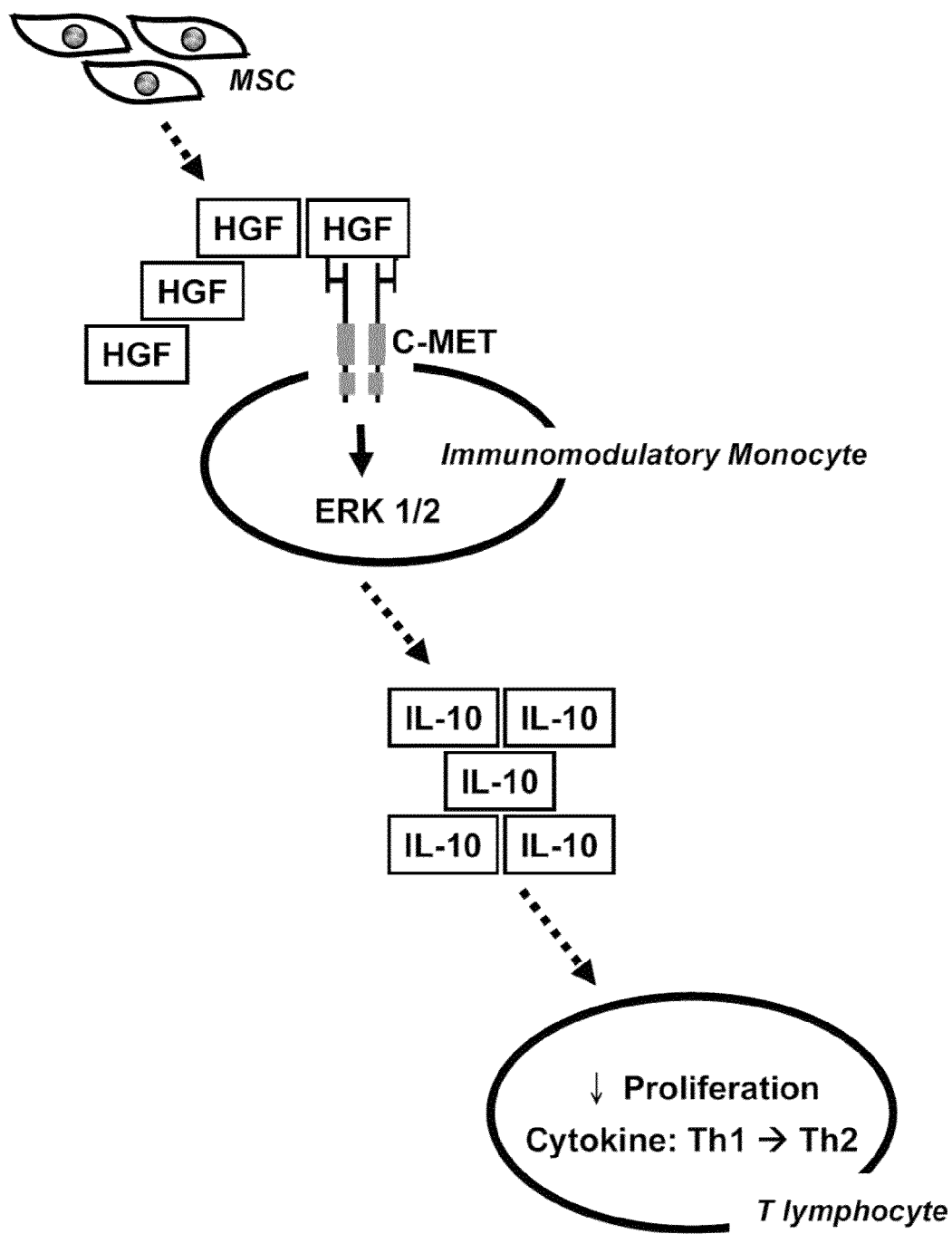
FIG. 12 shows mechanism of HGF-induced IL-10 production in CD14+ monocytes.

As shown in FIG. 12, HGF (especially secreted by MSCs) acts on CD14+ monocytes to modulate allogeneic T cell function and enhance IL-10 via ERK1/2. MSC-secreted HGF acts directly on CD14+ monocytes—which express c-Met, the receptor for HGF—to suppress activated CD4+ cell proliferation. These CD14+ monocytes are required for the suppressive effects of MSC-secreted HGF on activated CD4+ cells, including increasing the fraction of immunomodulatory CD14+CD16– monocytes, inducing IL-10 production, as well as modulating T cell cytokine profile from a Th1 to Th2 profile. Mechanistically, HGF induces IL-10 production by CD14+ monocytes through the ERK1/2 pathway. The above examples shed light on one of the mechanisms behind the strong immunomodulatory properties of MSCs, as well as highlight the important role of immunomodulatory monocytes in altering T cell effector function.

Interestingly, the suppressive effects of HGF on T cell proliferation are not dose-dependent, and this may be due to the low expression level of its receptor c-Met on monocytes, which likely result in a relatively low threshold of receptor saturation.

HGF induces phosphorylation of ERK1/2 and p38MAPK in monocytes and HGF-induced IL-10 production is only blocked by ERK1/2 inhibitor, suggesting that Ras/Raf signaling pathway is involved in HGF-induced IL-10 secretion by monocytes. ERK1/2 is responsible for the phosphorylation and activation of several transcription factors controlling IL-10 expression in immune cells, including MAF, JUN, GATA3 and SMAD4, which are not substrates for p38. Therefore, these transcription factors may have a critical role in HGF-induced IL-10 production in monocytes.

The above examples demonstrate that HGF can induce an immunomodulatory phenotype directly and very rapidly in CD14+ monocytes (within 3 days) with cells remaining non-adherant, suggesting that no differentiation has yet occurred. A subset of circulating peripheral blood monocytes which are CD14++CD16− can produce higher levels of anti-inflammatory cytokines, including IL-10. Circulating CD14+ monocytes are a large component of PBLs, and if immunoregulatory monocytes can be rapidly induced, these leukocytes could make a significant contribution to the amount of circulating immunoregulatory cells overall.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims and its equivalent systems and methods.

We claim:

1. A method for generating immunomodulatory cells comprising treating peripheral mononuclear cells with a hepatocyte growth factor (HGF) to induce differentiation of the peripheral mononuclear cells into immunomodulatory leukocytes,
wherein the concentration of the HGF is 3 to 40 ng/ml, and
wherein the immunomodulatory cells comprise a myeloid-derived suppressor cell exhibiting $CD14^-CD11b^+CD33^+$, a monocyte exhibiting $CD14^+CD16^-IL10^+$, or a combination thereof.

2. The method of claim 1, wherein the peripheral mononuclear cells are from a mammal.

3. The method of claim 1, wherein the hepatocyte growth factor is a recombinant protein or a natural protein.

4. The method of claim 3, wherein the hepatocyte growth factor is from a mesenchymal stem cell (MSC).

5. The method of claim 1, wherein the immunomodulatory leukocyte suppresses proliferation of an activated allogeneic lymphocyte.

6. The method of claim 1, wherein the myeloid-derived suppressor cell produces arginase and nitric oxide synthase.

7. The method of claim 1, wherein the myeloid-derived suppressor cell induces regulatory T cells.

8. The method of claim 1, wherein the monocyte produces IL-10.

9. The method of claim 1, wherein the monocyte produces an anti-inflammatory cytokine.

10. The method of claim 1, wherein the monocyte modulates immune response toward Th2-dominant response.

11. An immunomodulatory cell population prepared according to claim 1, which contains $CD14^-CD11b^+CD33^+$ myeloid-derived suppressor cells and $CD14^+CD16^-IL10^+$ monocytes.

* * * * *